(12) United States Patent
Globerman et al.

(10) Patent No.: US 9,381,024 B2
(45) Date of Patent: Jul. 5, 2016

(54) MARKED TOOLS

(75) Inventors: Oren Globerman, Kfar-Shmaryahu (IL); Mordechay Beyar, Caesarea (IL)

(73) Assignee: DePuy Synthes Products, Inc., Raynham, MA (US)

( * ) Notice: Subject to any disclaimer, the term of this patent is extended or adjusted under 35 U.S.C. 154(b) by 2696 days.

(21) Appl. No.: 11/536,355

(22) Filed: Sep. 28, 2006

(65) Prior Publication Data
US 2008/0200915 A1    Aug. 21, 2008

Related U.S. Application Data

(63) Continuation-in-part of application No. PCT/IL2005/000812, filed on Jul. 31, 2005, and a continuation-in-part of application No. 11/194,411, filed on Aug. 1, 2005.

(60) Provisional application No. 60/720,725, filed on Sep. 28, 2005.

(51) Int. Cl.
| | | |
|---|---|---|
| *A61B 17/00* | (2006.01) | |
| *A61B 17/16* | (2006.01) | |
| *A61B 17/34* | (2006.01) | |
| *A61B 17/88* | (2006.01) | |

(52) U.S. Cl.
CPC .......... *A61B 17/1637* (2013.01); *A61B 17/1671* (2013.01); *A61B 17/3472* (2013.01); *A61B 17/8802* (2013.01); *A61B 2017/00539* (2013.01); *A61B 2017/00902* (2013.01)

(58) Field of Classification Search
USPC ......... 606/79, 80, 84, 86 A, 88–92, 279, 914; 623/17.11–17.16
See application file for complete search history.

(56) References Cited

U.S. PATENT DOCUMENTS

| | | |
|---|---|---|
| 229,932 A | 7/1880 | Witsil |
| 370,335 A | 9/1887 | Hunter |
| 817,973 A | 4/1906 | Hausmann |

(Continued)

FOREIGN PATENT DOCUMENTS

| | | |
|---|---|---|
| AU | 724544 | 11/1996 |
| AU | 9865136 | 9/1998 |

(Continued)

OTHER PUBLICATIONS

Baroud et al. "Injection Biomechanics of Bone Cements Used in Vertebroplasty", Biomedical Maerials and Engineering, 00: 1-18, 2004.

(Continued)

*Primary Examiner* — Sameh Boles
(74) *Attorney, Agent, or Firm* — Nutter McClennen & Fish LLP

(57) ABSTRACT

A surgical apparatus, the apparatus comprising: (a) a cutting tool comprising an axial member with a proximal end and a distal end, the axial member characterized by at least two adjacent axial sections, wherein differences between each of the sections are visually discernible when viewed in a projection x-ray image; and (b) a hollow tube adapted for parallel alignment with the cutting tool and selectively axially positionable to be adjacent at least a selective one of said axial sections and block x-ray radiation from at least one of passing through or passing adjacent said selected section so that said projection indicates a relative axial position of said hollow tube and said cutting tool.

21 Claims, 10 Drawing Sheets

(56) References Cited

U.S. PATENT DOCUMENTS

| | | |
|---|---|---|
| 833,044 A | 10/1906 | Goodhugh |
| 843,587 A | 2/1907 | DePew |
| 1,175,530 A | 3/1916 | Kirchhoff |
| 1,612,281 A | 12/1926 | Goetz |
| 1,612,996 A | 1/1927 | Waagbo |
| 1,733,516 A | 10/1929 | Jamison |
| 1,894,274 A | 1/1933 | Jacques |
| 1,929,247 A | 10/1933 | Hein |
| 2,123,712 A | 7/1938 | Clark |
| 2,283,915 A | 5/1942 | Cole |
| 2,394,488 A | 2/1946 | Rotter et al. |
| 2,425,867 A | 8/1947 | Davis |
| 2,435,647 A | 2/1948 | Engseth |
| 2,497,762 A | 2/1950 | Davis |
| 2,521,569 A | 9/1950 | Davis |
| 2,567,960 A | 9/1951 | Meyers et al. |
| 2,745,575 A | 5/1956 | Spencer |
| 2,773,500 A | 12/1956 | Young |
| 2,808,239 A | 10/1957 | Alfred |
| 2,874,877 A | 2/1959 | Spencer |
| 2,918,841 A | 12/1959 | Poupitch |
| 2,928,574 A | 3/1960 | Wagner |
| 2,970,773 A | 2/1961 | Horace et al. |
| 3,058,413 A | 10/1962 | Cavalieri |
| 3,063,449 A | 11/1962 | Schultz |
| 3,075,746 A | 1/1963 | Yablonski et al. |
| 3,108,593 A | 10/1963 | Glassman |
| 3,151,847 A | 10/1964 | Broomall |
| 3,198,194 A | 8/1965 | Wilburn |
| 3,216,616 A | 11/1965 | Blankenship, Jr. |
| 3,224,744 A | 12/1965 | Broomall |
| 3,225,760 A | 12/1965 | Di Cosola |
| 3,254,494 A | 6/1966 | Chartouni |
| 3,362,793 A | 1/1968 | Massoubre |
| 3,381,566 A | 5/1968 | Passer |
| 3,426,364 A | 2/1969 | Lumb |
| 3,515,873 A | 6/1970 | Higgins |
| 3,559,956 A | 2/1971 | Gray |
| 3,568,885 A | 3/1971 | Spencer |
| 3,572,556 A | 3/1971 | Pogacar |
| 3,615,240 A | 10/1971 | Sanz |
| 3,674,011 A | 7/1972 | Michel et al. |
| 3,701,350 A | 10/1972 | Guenther |
| 3,750,667 A | 8/1973 | Pshenichny et al. |
| 3,789,727 A | 2/1974 | Moran |
| 3,796,303 A | 3/1974 | Allet-Coche |
| 3,798,982 A | 3/1974 | Lundquist |
| 3,846,846 A | 11/1974 | Fischer |
| 3,850,158 A | 11/1974 | Elias et al. |
| 3,867,728 A | 2/1975 | Stubstad et al. |
| 3,873,008 A | 3/1975 | Jahn |
| 3,875,595 A | 4/1975 | Froning |
| 3,896,504 A | 7/1975 | Fischer |
| 3,901,408 A | 8/1975 | Boden et al. |
| 3,921,858 A | 11/1975 | Bemm |
| 3,931,914 A | 1/1976 | Hosaka et al. |
| 3,942,407 A | 3/1976 | Mortensen |
| 3,976,060 A | 8/1976 | Hildebrandt et al. |
| 3,993,250 A | 11/1976 | Shure |
| 4,011,602 A | 3/1977 | Rybicki et al. |
| 4,062,274 A | 12/1977 | Knab |
| 4,077,494 A | 3/1978 | Spaude et al. |
| 4,079,917 A | 3/1978 | Popeil |
| 4,090,640 A | 5/1978 | Smith et al. |
| 4,093,576 A | 6/1978 | Dewijn |
| 4,105,145 A | 8/1978 | Capra |
| 4,115,346 A | 9/1978 | Gross et al. |
| 4,146,334 A | 3/1979 | Farrell |
| 4,168,787 A | 9/1979 | Stamper |
| 4,170,990 A | 10/1979 | Baumgart et al. |
| 4,180,070 A | 12/1979 | Genese |
| 4,185,072 A | 1/1980 | Puderbaugh et al. |
| 4,189,065 A | 2/1980 | Herold |
| 4,198,383 A | 4/1980 | Konsetov et al. |
| 4,198,975 A | 4/1980 | Haller |
| 4,204,531 A | 5/1980 | Aginsky |
| 4,239,113 A | 12/1980 | Gross et al. |
| 4,250,887 A | 2/1981 | Dardik et al. |
| 4,257,540 A | 3/1981 | Wegmann et al. |
| 4,268,639 A | 5/1981 | Seidel et al. |
| 4,274,163 A | 6/1981 | Malcom et al. |
| 4,276,878 A | 7/1981 | Storz |
| 4,277,184 A | 7/1981 | Solomon |
| 4,298,144 A | 11/1981 | Pressl |
| 4,309,777 A | 1/1982 | Patil |
| 4,312,343 A | 1/1982 | LeVeen et al. |
| 4,313,434 A | 2/1982 | Segal |
| 4,326,567 A | 4/1982 | Mistarz |
| 4,338,925 A | 7/1982 | Miller |
| 4,341,691 A | 7/1982 | Anuta |
| 4,346,708 A | 8/1982 | LeVeen et al. |
| 4,349,921 A | 9/1982 | Kuntz |
| 4,359,049 A | 11/1982 | Redl et al. |
| 4,373,217 A | 2/1983 | Draenert |
| 4,380,398 A | 4/1983 | Burgess |
| 4,400,170 A | 8/1983 | McNaughton et al. |
| 4,403,989 A | 9/1983 | Christensen et al. |
| 4,404,327 A | 9/1983 | Crugnola et al. |
| 4,405,249 A | 9/1983 | Scales |
| 4,409,966 A | 10/1983 | Lambrecht et al. |
| 4,453,539 A | 6/1984 | Raftopoulos et al. |
| 4,474,572 A | 10/1984 | McNaughton et al. |
| 4,475,856 A | 10/1984 | Toomingas |
| 4,476,866 A | 10/1984 | Chin |
| 4,487,602 A | 12/1984 | Christensen et al. |
| 4,494,535 A | 1/1985 | Haig |
| 4,500,658 A | 2/1985 | Fox |
| 4,503,169 A | 3/1985 | Randklev |
| 4,522,200 A | 6/1985 | Stednitz |
| D279,499 S | 7/1985 | Case |
| 4,543,966 A | 10/1985 | Islam et al. |
| 4,546,767 A | 10/1985 | Smith |
| 4,554,914 A | 11/1985 | Kapp et al. |
| 4,558,693 A | 12/1985 | Lash et al. |
| 4,562,598 A | 1/1986 | Kranz |
| 4,576,152 A | 3/1986 | Muller et al. |
| 4,588,583 A | 5/1986 | Pietsch et al. |
| 4,593,685 A | 6/1986 | McKay et al. |
| 4,595,006 A | 6/1986 | Burke et al. |
| 4,600,118 A | 7/1986 | Martin |
| 4,605,011 A | 8/1986 | Naslund |
| 4,632,101 A | 12/1986 | Freedland |
| 4,636,217 A | 1/1987 | Ogilvie et al. |
| 4,642,099 A | 2/1987 | Phillips et al. |
| 4,650,469 A | 3/1987 | Berg et al. |
| 4,651,904 A | 3/1987 | Schuckmann |
| 4,653,487 A | 3/1987 | Maale |
| 4,653,489 A | 3/1987 | Tronzo et al. |
| 4,664,298 A | 5/1987 | Shew |
| 4,664,655 A | 5/1987 | Orentreich et al. |
| 4,668,220 A | 5/1987 | Hawrylenko |
| 4,668,295 A | 5/1987 | Bajpai |
| 4,670,008 A | 6/1987 | Von Albertini |
| 4,671,263 A | 6/1987 | Draenert |
| 4,676,655 A | 6/1987 | Handler |
| 4,676,781 A | 6/1987 | Phillips et al. |
| 4,686,973 A | 8/1987 | Frisch |
| 4,697,584 A | 10/1987 | Haynes |
| 4,697,929 A | 10/1987 | Muller |
| 4,704,035 A | 11/1987 | Kowalczyk |
| 4,710,179 A | 12/1987 | Haber et al. |
| 4,714,721 A | 12/1987 | Franek et al. |
| 4,717,383 A | 1/1988 | Phillips et al. |
| 4,718,910 A | 1/1988 | Draenert |
| 4,722,948 A | 2/1988 | Sanderson |
| 4,735,616 A | 4/1988 | Eibl et al. |
| 4,737,151 A | 4/1988 | Clement et al. |
| 4,747,832 A | 5/1988 | Buffet |
| 4,758,096 A | 7/1988 | Gunnarsson |
| 4,758,234 A | 7/1988 | Orentreich et al. |
| 4,759,769 A | 7/1988 | Hedman et al. |
| 4,762,515 A | 8/1988 | Grimm |
| 4,767,033 A | 8/1988 | Gemperle |
| 4,772,287 A | 9/1988 | Ray et al. |

(56) References Cited

U.S. PATENT DOCUMENTS

| | | |
|---|---|---|
| 4,782,118 A | 11/1988 | Fontanille et al. |
| 4,786,184 A | 11/1988 | Berezkina et al. |
| 4,791,150 A | 12/1988 | Braden et al. |
| 4,792,577 A | 12/1988 | Chen et al. |
| 2,067,458 A | 2/1989 | Nichols |
| 4,804,023 A | 2/1989 | Frearson |
| 4,813,870 A | 3/1989 | Pitzen |
| 4,815,454 A | 3/1989 | Dozier |
| 4,815,632 A | 3/1989 | Ball et al. |
| 4,826,053 A | 5/1989 | Keller |
| 4,830,227 A | 5/1989 | Ball et al. |
| 4,837,279 A | 6/1989 | Arroyo |
| 4,854,312 A | 8/1989 | Raftopoulos et al. |
| 4,854,482 A | 8/1989 | Bergner |
| 4,854,716 A | 8/1989 | Ziemann et al. |
| 4,863,072 A | 9/1989 | Perler |
| 4,869,906 A | 9/1989 | Dingeldein et al. |
| 4,872,936 A | 10/1989 | Engelbrecht |
| 4,892,231 A | 1/1990 | Ball |
| 4,892,550 A | 1/1990 | Huebsch |
| 4,902,649 A | 2/1990 | Kimura et al. |
| 4,904,260 A | 2/1990 | Ray et al. |
| 4,908,017 A | 3/1990 | Howson et al. |
| 4,910,259 A | 3/1990 | Kindt-Larsen et al. |
| 4,927,866 A | 5/1990 | Purrmann et al. |
| 4,932,969 A | 6/1990 | Frey et al. |
| 4,935,029 A | 6/1990 | Matsutani et al. |
| 4,944,065 A | 7/1990 | Svanberg et al. |
| 4,944,726 A | 7/1990 | Hilal et al. |
| 4,946,077 A | 8/1990 | Olsen |
| 4,946,285 A | 8/1990 | Vennemeyer |
| 4,946,901 A | 8/1990 | Lechner et al. |
| 4,961,647 A | 10/1990 | Coutts et al. |
| 4,966,601 A | 10/1990 | Draenert |
| 4,968,303 A | 11/1990 | Clarke et al. |
| 4,969,888 A | 11/1990 | Scholten et al. |
| 4,973,168 A | 11/1990 | Chan |
| 4,973,301 A | 11/1990 | Nissenkorn |
| 4,973,334 A | 11/1990 | Ziemann |
| 4,978,336 A | 12/1990 | Capozzi et al. |
| 4,983,164 A | 1/1991 | Hook et al. |
| 4,994,065 A | 2/1991 | Gibbs et al. |
| 4,995,868 A | 2/1991 | Brazier |
| 5,004,501 A | 4/1991 | Faccioli et al. |
| 5,006,112 A | 4/1991 | Metzner |
| 5,012,066 A | 4/1991 | Matsutani et al. |
| 5,015,233 A | 5/1991 | McGough et al. |
| 5,018,919 A | 5/1991 | Stephan |
| 5,022,563 A | 6/1991 | Marchitto et al. |
| 5,024,232 A | 6/1991 | Smid et al. |
| 5,028,141 A | 7/1991 | Stiegelmann |
| 5,037,473 A | 8/1991 | Antonucci et al. |
| 5,049,157 A | 9/1991 | Mittelmeier et al. |
| 5,051,482 A | 9/1991 | Tepic |
| 5,059,193 A | 10/1991 | Kuslich |
| 5,059,199 A | 10/1991 | Okada et al. |
| 5,061,128 A | 10/1991 | Jahr et al. |
| 5,062,128 A | 10/1991 | Katsuragi et al. |
| 5,071,040 A | 12/1991 | Laptewicz, Jr. |
| 5,074,871 A | 12/1991 | Groshong |
| 5,078,919 A | 1/1992 | Ashley et al. |
| 5,092,888 A | 3/1992 | Iwamoto et al. |
| 5,102,413 A | 4/1992 | Poddar |
| 5,108,403 A | 4/1992 | Stern |
| 5,108,404 A | 4/1992 | Scholten et al. |
| 5,112,333 A | 5/1992 | Fixel |
| 5,114,240 A | 5/1992 | Kindt-Larsen et al. |
| 5,116,335 A | 5/1992 | Hannon |
| 5,122,400 A | 6/1992 | Stewart |
| 5,123,926 A | 6/1992 | Pisharodi |
| 5,125,971 A | 6/1992 | Nonami et al. |
| 5,131,382 A | 7/1992 | Meyer |
| 5,141,496 A | 8/1992 | Dalto et al. |
| 5,145,250 A | 9/1992 | Planck et al. |
| 5,147,903 A | 9/1992 | Podszun et al. |
| 5,171,248 A | 12/1992 | Ellis |
| 5,171,278 A | 12/1992 | Pisharodi |
| 5,181,918 A | 1/1993 | Brandhorst et al. |
| 5,188,259 A | 2/1993 | Petit |
| 5,190,191 A | 3/1993 | Reyman |
| 5,192,327 A | 3/1993 | Brantigan |
| 5,193,907 A | 3/1993 | Faccioli |
| 5,209,753 A | 5/1993 | Biedermann et al. |
| 5,217,147 A | 6/1993 | Kaufman |
| 5,219,897 A | 6/1993 | Murray |
| 5,236,445 A | 8/1993 | Hayhurst et al. |
| 5,242,983 A | 9/1993 | Kennedy et al. |
| 5,252,301 A | 10/1993 | Nilson et al. |
| 5,254,092 A | 10/1993 | Polyak |
| 5,258,420 A | 11/1993 | Posey-Dowty et al. |
| 5,264,215 A | 11/1993 | Nakabayashi et al. |
| 5,268,001 A | 12/1993 | Nicholson et al. |
| 5,269,762 A | 12/1993 | Armbruster et al. |
| 5,275,214 A | 1/1994 | Rehberger |
| 5,276,070 A | 1/1994 | Arroyo |
| 5,277,339 A | 1/1994 | Shew et al. |
| 5,279,555 A | 1/1994 | Lifshey |
| 5,290,260 A | 3/1994 | Stines |
| 5,295,980 A | 3/1994 | Ersek |
| 5,302,020 A | 4/1994 | Kruse |
| 5,303,718 A | 4/1994 | Kajicek |
| 5,304,147 A | 4/1994 | Johnson et al. |
| 5,318,532 A | 6/1994 | Frassica |
| 5,328,262 A | 7/1994 | Lidgren et al. |
| 5,328,362 A | 7/1994 | Watson et al. |
| 5,331,972 A | 7/1994 | Wadhwani et al. |
| 5,333,951 A | 8/1994 | Wakoh |
| 5,334,184 A | 8/1994 | Bimman |
| 5,334,626 A | 8/1994 | Lin |
| 5,336,699 A | 8/1994 | Cooke et al. |
| 5,336,700 A | 8/1994 | Murray |
| 5,344,232 A | 9/1994 | Nelson et al. |
| 5,348,391 A | 9/1994 | Murray |
| 5,348,548 A | 9/1994 | Meyer et al. |
| 5,350,372 A | 9/1994 | Ikeda et al. |
| 5,354,287 A | 10/1994 | Wacks |
| 5,356,382 A | 10/1994 | Picha et al. |
| 5,368,046 A | 11/1994 | Scarfone et al. |
| 5,368,386 A | 11/1994 | Murray |
| 5,370,221 A | 12/1994 | Magnusson et al. |
| 5,372,583 A | 12/1994 | Roberts et al. |
| 5,374,427 A | 12/1994 | Stille et al. |
| 5,375,583 A | 12/1994 | Meyer et al. |
| 5,376,123 A | 12/1994 | Klaue et al. |
| 5,380,772 A | 1/1995 | Hasegawa et al. |
| 5,385,081 A | 1/1995 | Sneddon |
| 5,385,566 A | 1/1995 | Ullmark |
| 5,387,191 A | 2/1995 | Hemstreet et al. |
| 5,390,683 A | 2/1995 | Pisharodi |
| 5,395,167 A | 3/1995 | Murray |
| 5,395,326 A | 3/1995 | Haber et al. |
| 5,398,483 A | 3/1995 | Smith et al. |
| 5,401,806 A | 3/1995 | Braden et al. |
| 5,407,266 A | 4/1995 | Dotsch et al. |
| 5,411,180 A | 5/1995 | Dumelle |
| 5,415,474 A | 5/1995 | Nelson et al. |
| 5,423,824 A | 6/1995 | Akerfeldt et al. |
| 5,423,850 A | 6/1995 | Berger |
| 5,431,654 A | 7/1995 | Nic |
| 5,435,645 A | 7/1995 | Faccioli |
| 5,441,502 A | 8/1995 | Bartlett |
| 5,443,182 A | 8/1995 | Tanaka et al. |
| 5,445,639 A | 8/1995 | Kuslich et al. |
| 5,450,924 A | 9/1995 | Tseng |
| 5,454,365 A | 10/1995 | Bonutti |
| 5,456,267 A | 10/1995 | Stark |
| 5,468,245 A | 11/1995 | Vargas, III |
| 5,480,400 A | 1/1996 | Berger |
| 5,480,403 A | 1/1996 | Lee |
| 5,482,187 A | 1/1996 | Poulsen et al. |
| 5,492,247 A | 2/1996 | Shu et al. |
| 5,494,349 A | 2/1996 | Seddon |
| 5,501,374 A | 3/1996 | Laufer et al. |
| 5,501,520 A | 3/1996 | Lidgren et al. |

(56) References Cited

U.S. PATENT DOCUMENTS

| | | | |
|---|---|---|---|
| 5,501,695 A | 3/1996 | Anspach, Jr. et al. |
| 5,512,610 A | 4/1996 | Lin |
| 5,514,135 A | 5/1996 | Earle |
| 5,514,137 A | 5/1996 | Coutts |
| 5,518,498 A | 5/1996 | Lindenberg et al. |
| 5,520,690 A | 5/1996 | Errico et al. |
| 5,522,816 A | 6/1996 | Dinello et al. |
| 5,522,899 A | 6/1996 | Michelson |
| 5,526,853 A | 6/1996 | McPhee et al. |
| 5,531,519 A | 7/1996 | Earle |
| 5,534,028 A | 7/1996 | Bao et al. |
| 5,536,262 A | 7/1996 | Velasquez |
| 5,545,460 A | 8/1996 | Tanaka et al. |
| 5,548,001 A | 8/1996 | Podszun et al. |
| 5,549,380 A | 8/1996 | Lidgren et al. |
| 5,549,381 A | 8/1996 | Hays et al. |
| 5,549,679 A | 8/1996 | Kuslich |
| 5,551,778 A | 9/1996 | Hauke et al. |
| 5,554,101 A | 9/1996 | Matula et al. |
| 5,556,201 A | 9/1996 | Veltrop et al. |
| 5,558,136 A | 9/1996 | Orrico |
| 5,558,639 A | 9/1996 | Gangemi et al. |
| 5,571,189 A | 11/1996 | Kuslich et al. |
| 5,573,265 A | 11/1996 | Pradel |
| 5,578,035 A | 11/1996 | Lin |
| 5,586,821 A | 12/1996 | Bonitati et al. |
| 5,588,745 A | 12/1996 | Tanaka et al. |
| 5,591,197 A | 1/1997 | Orth et al. |
| 5,601,557 A | 2/1997 | Hayhurst |
| 5,603,701 A | 2/1997 | Fischer |
| 5,609,637 A | 3/1997 | Biedermann et al. |
| 5,624,184 A | 4/1997 | Chan |
| 5,630,806 A * | 5/1997 | Inagaki et al. ................ 604/524 |
| 5,634,880 A | 6/1997 | Feldman et al. |
| 5,637,097 A | 6/1997 | Yoon |
| 5,638,997 A | 6/1997 | Hawkins et al. |
| 5,641,010 A | 6/1997 | Maier |
| 5,645,598 A | 7/1997 | Brosnahan, III |
| 5,647,856 A | 7/1997 | Eykmann |
| 5,653,686 A | 8/1997 | Coulter et al. |
| 5,658,310 A | 8/1997 | Berger |
| 5,660,186 A | 8/1997 | Bachir |
| 5,665,067 A | 9/1997 | Linder et al. |
| 5,681,317 A | 10/1997 | Caldarise |
| 5,683,451 A | 11/1997 | Lenker et al. |
| 5,685,826 A | 11/1997 | Bonutti |
| 5,690,606 A | 11/1997 | Slotman |
| 5,693,100 A | 12/1997 | Pisharodi |
| 5,697,977 A | 12/1997 | Pisharodi |
| 5,698,611 A | 12/1997 | Okada et al. |
| 5,702,448 A | 12/1997 | Buechel et al. |
| 5,704,895 A | 1/1998 | Scott et al. |
| 5,707,390 A | 1/1998 | Bonutti |
| 5,718,707 A | 2/1998 | Mikhail |
| 5,720,753 A | 2/1998 | Sander et al. |
| 5,725,341 A | 3/1998 | Hofmeister |
| 5,725,529 A | 3/1998 | Nicholson et al. |
| 5,747,553 A | 5/1998 | Guzauskas |
| 5,752,935 A | 5/1998 | Robinson et al. |
| 5,752,969 A | 5/1998 | Cunci |
| 5,752,974 A | 5/1998 | Rhee |
| 5,755,732 A | 5/1998 | Green et al. |
| 5,759,186 A | 6/1998 | Bachmann et al. |
| 5,763,092 A | 6/1998 | Lee et al. |
| 5,779,356 A | 7/1998 | Chan |
| 5,782,713 A | 7/1998 | Yang |
| 5,782,747 A | 7/1998 | Zimmon |
| 5,782,830 A | 7/1998 | Farris |
| 5,782,838 A | 7/1998 | Beyar et al. |
| 5,785,647 A | 7/1998 | Tompkins et al. |
| 5,792,044 A | 8/1998 | Foley |
| 5,795,922 A | 8/1998 | Demian et al. |
| 5,797,678 A | 8/1998 | Murray |
| 5,800,169 A | 9/1998 | Muhlbauer |
| 5,800,409 A | 9/1998 | Bruce |
| 5,800,549 A | 9/1998 | Bao et al. |
| 5,800,550 A | 9/1998 | Sertich |
| 5,820,321 A | 10/1998 | Gruber |
| 5,824,087 A | 10/1998 | Aspden et al. |
| 5,826,713 A | 10/1998 | Sunago et al. |
| 5,826,753 A | 10/1998 | Fehlig et al. |
| 5,827,217 A | 10/1998 | Silver et al. |
| 5,827,289 A | 10/1998 | Reiley et al. |
| 5,829,875 A | 11/1998 | Hagel et al. |
| 5,830,194 A | 11/1998 | Anwar et al. |
| 5,836,306 A | 11/1998 | Duane et al. |
| 5,839,621 A | 11/1998 | Tada |
| 5,842,785 A | 12/1998 | Brown et al. |
| 5,865,802 A | 2/1999 | Yoon et al. |
| 5,876,116 A | 3/1999 | Barker et al. |
| 5,876,457 A | 3/1999 | Picha et al. |
| 5,882,340 A | 3/1999 | Yoon et al. |
| 5,884,818 A | 3/1999 | Campbell |
| 5,893,488 A | 4/1999 | Hoag et al. |
| 5,893,850 A | 4/1999 | Cachia |
| 5,902,839 A | 5/1999 | Lautenschlager et al. |
| 5,911,721 A | 6/1999 | Nicholson et al. |
| 5,918,702 A | 7/1999 | Cheng et al. |
| 5,918,770 A | 7/1999 | Camm et al. |
| 5,925,051 A | 7/1999 | Mikhail |
| 5,928,239 A | 7/1999 | Mirza |
| 5,931,347 A | 8/1999 | Haubrich |
| 5,941,851 A | 8/1999 | Coffey et al. |
| 5,954,671 A | 9/1999 | O'Neill |
| 5,954,728 A | 9/1999 | Heller et al. |
| 5,961,211 A | 10/1999 | Barker et al. |
| 5,968,008 A | 10/1999 | Grams |
| 5,968,044 A | 10/1999 | Nicholson et al. |
| 5,968,999 A | 10/1999 | Ramp et al. |
| 5,972,015 A | 10/1999 | Scribner et al. |
| 5,980,527 A | 11/1999 | Cohen et al. |
| 5,993,535 A | 11/1999 | Sawamura et al. |
| 5,997,544 A | 12/1999 | Nies et al. |
| 6,004,325 A | 12/1999 | Vargas, III |
| 6,007,496 A | 12/1999 | Brannon |
| 6,017,349 A | 1/2000 | Heller et al. |
| 6,019,765 A | 2/2000 | Thornhill et al. |
| 6,019,776 A | 2/2000 | Preissman et al. |
| 6,019,789 A | 2/2000 | Dinh et al. |
| 6,020,396 A | 2/2000 | Jacobs |
| 6,033,105 A | 3/2000 | Barker et al. |
| 6,033,411 A | 3/2000 | Preissman |
| 6,039,761 A | 3/2000 | Li et al. |
| 6,040,408 A | 3/2000 | Koole |
| 6,041,977 A | 3/2000 | Lisi |
| 6,042,262 A | 3/2000 | Hajianpour |
| 6,045,555 A | 4/2000 | Smith et al. |
| 6,048,346 A | 4/2000 | Reiley |
| 6,049,026 A | 4/2000 | Muschler |
| 6,075,067 A | 6/2000 | Lidgren |
| 6,080,579 A | 6/2000 | Hanley, Jr. |
| 6,080,801 A | 6/2000 | Draenert et al. |
| 6,080,811 A | 6/2000 | Schehlmann et al. |
| 6,083,229 A | 7/2000 | Constantz et al. |
| 6,086,594 A | 7/2000 | Brown |
| 6,103,779 A | 8/2000 | Guzauskas |
| 6,116,773 A | 9/2000 | Murray |
| 6,120,174 A | 9/2000 | Hoag et al. |
| 6,124,373 A | 9/2000 | Peter et al. |
| 6,126,689 A | 10/2000 | Brett |
| 6,127,597 A | 10/2000 | Beyar et al. |
| 6,129,763 A | 10/2000 | Chauvin et al. |
| 6,132,396 A | 10/2000 | Antanavich et al. |
| 6,136,038 A | 10/2000 | Raab |
| 6,139,509 A | 10/2000 | Yuan et al. |
| 6,142,998 A | 11/2000 | Smith et al. |
| 6,146,401 A | 11/2000 | Yoon et al. |
| 6,149,651 A | 11/2000 | Drewry et al. |
| 6,149,655 A | 11/2000 | Constantz et al. |
| 6,149,664 A | 11/2000 | Kurz |
| 6,160,033 A | 12/2000 | Nies |
| 6,161,955 A | 12/2000 | Rademaker |
| 6,168,597 B1 | 1/2001 | Biedermann et al. |
| 6,174,935 B1 | 1/2001 | Matsunae et al. |

(56) References Cited

U.S. PATENT DOCUMENTS

| | | |
|---|---|---|
| 6,176,607 B1 | 1/2001 | Hajianpour |
| 6,183,441 B1 | 2/2001 | Kriesel et al. |
| 6,183,516 B1 | 2/2001 | Burkinshaw et al. |
| 6,187,015 B1 | 2/2001 | Brenneman |
| 6,190,381 B1 | 2/2001 | Olsen et al. |
| 6,210,031 B1 | 4/2001 | Murray |
| 6,214,012 B1 | 4/2001 | Karpman et al. |
| 6,214,016 B1 | 4/2001 | Williams et al. |
| 6,214,037 B1 | 4/2001 | Mitchell et al. |
| 6,217,566 B1 | 4/2001 | Ju et al. |
| 6,217,581 B1 | 4/2001 | Tolson |
| 6,217,608 B1 | 4/2001 | Penn et al. |
| 6,221,029 B1 | 4/2001 | Mathis et al. |
| 6,224,604 B1 | 5/2001 | Suddaby |
| 6,228,049 B1 | 5/2001 | Schroeder et al. |
| 6,228,068 B1 | 5/2001 | Yoon |
| 6,228,082 B1 | 5/2001 | Baker et al. |
| 6,231,615 B1 | 5/2001 | Preissman |
| 6,235,043 B1 | 5/2001 | Reiley et al. |
| 6,238,399 B1 | 5/2001 | Heller et al. |
| 6,241,734 B1 * | 6/2001 | Scribner et al. ............. 606/93 |
| 6,245,101 B1 | 6/2001 | Drasler et al. |
| 6,248,110 B1 | 6/2001 | Reiley et al. |
| 6,254,268 B1 | 7/2001 | Long |
| 6,261,289 B1 | 7/2001 | Levy |
| 6,264,618 B1 | 7/2001 | Landi et al. |
| 6,264,659 B1 | 7/2001 | Ross et al. |
| 6,264,660 B1 | 7/2001 | Schmidt et al. |
| 6,273,916 B1 | 8/2001 | Murphy |
| 6,281,271 B1 | 8/2001 | Rumphorst et al. |
| 6,309,395 B1 | 10/2001 | Smith et al. |
| 6,309,420 B1 | 10/2001 | Preissman |
| 6,312,149 B1 | 11/2001 | Sjovall et al. |
| 6,325,812 B1 | 12/2001 | Dubrul et al. |
| 6,348,055 B1 | 2/2002 | Preissman |
| 6,348,518 B1 | 2/2002 | Montgomery |
| 6,350,271 B1 | 2/2002 | Kurz et al. |
| 6,361,539 B1 | 3/2002 | Heller et al. |
| 6,364,865 B1 | 4/2002 | Lavi et al. |
| 6,367,962 B1 | 4/2002 | Mizutani et al. |
| 6,375,659 B1 | 4/2002 | Erbe et al. |
| 6,375,682 B1 | 4/2002 | Fleischmann et al. |
| 6,383,188 B2 | 5/2002 | Kuslich et al. |
| 6,383,190 B1 | 5/2002 | Preissman |
| 6,395,007 B1 | 5/2002 | Bhatnagar |
| 6,402,701 B1 | 6/2002 | Kaplan et al. |
| 6,402,758 B1 | 6/2002 | Tolson |
| 6,406,175 B1 | 6/2002 | Marino |
| 6,409,972 B1 | 6/2002 | Chan |
| 6,410,612 B1 | 6/2002 | Hatanaka |
| 6,425,887 B1 | 7/2002 | McGuckin et al. |
| 6,431,743 B1 | 8/2002 | Mizutani et al. |
| 6,433,037 B1 | 8/2002 | Guzauskas |
| 6,436,143 B1 | 8/2002 | Ross et al. |
| 6,439,439 B1 | 8/2002 | Rickard |
| 6,443,334 B1 | 9/2002 | John et al. |
| 6,447,478 B1 | 9/2002 | Maynards |
| 6,450,973 B1 | 9/2002 | Murphy |
| 6,458,117 B1 | 10/2002 | Pollins, Sr. |
| 6,479,565 B1 | 11/2002 | Stanley |
| 6,488,667 B1 | 12/2002 | Murphy |
| 6,494,868 B2 | 12/2002 | Amar |
| 6,500,182 B2 | 12/2002 | Foster |
| 6,502,608 B1 | 1/2003 | Burchett et al. |
| 6,527,144 B2 | 3/2003 | Ritsche et al. |
| 6,550,957 B2 | 4/2003 | Mizutani et al. |
| 6,554,833 B2 | 4/2003 | Levy et al. |
| 6,572,256 B2 | 6/2003 | Seaton et al. |
| 6,575,331 B1 | 6/2003 | Peeler et al. |
| 6,575,919 B1 | 6/2003 | Reiley et al. |
| 6,582,439 B1 | 6/2003 | Sproul |
| 6,592,559 B1 | 7/2003 | Pakter et al. |
| 6,595,967 B2 | 7/2003 | Kramer |
| 6,599,293 B2 | 7/2003 | Tague et al. |
| 6,599,520 B2 | 7/2003 | Scarborough et al. |
| 6,613,018 B2 | 9/2003 | Bagga |
| 6,613,054 B2 | 9/2003 | Scribner et al. |
| 6,626,912 B2 | 9/2003 | Speitling |
| 6,641,587 B2 | 11/2003 | Scribner et al. |
| 6,645,213 B2 | 11/2003 | Sand et al. |
| 6,662,969 B2 | 12/2003 | Peeler et al. |
| 6,676,664 B1 | 1/2004 | Al-Assir |
| 6,689,823 B1 | 2/2004 | Bellare et al. |
| 6,702,455 B2 | 3/2004 | Vendrely et al. |
| 6,712,853 B2 | 3/2004 | Kuslich |
| 6,716,216 B1 | 4/2004 | Boucher et al. |
| 6,719,761 B1 | 4/2004 | Reiley et al. |
| 6,720,417 B1 | 4/2004 | Walter |
| 6,730,095 B2 | 5/2004 | Olson, Jr. et al. |
| 6,752,180 B2 | 6/2004 | Delay |
| 6,758,837 B2 | 7/2004 | Peciat et al. |
| 6,759,449 B2 | 7/2004 | Kimura et al. |
| 6,767,973 B2 | 7/2004 | Suau et al. |
| 6,770,079 B2 | 8/2004 | Bhatnagar |
| 6,779,566 B2 | 8/2004 | Engel |
| 6,780,175 B1 | 8/2004 | Sachdeva et al. |
| 6,783,515 B1 | 8/2004 | Miller et al. |
| 6,787,584 B2 | 9/2004 | Jia et al. |
| 6,796,987 B2 | 9/2004 | Tague et al. |
| 6,852,439 B2 | 2/2005 | Frank |
| 6,874,927 B2 | 4/2005 | Foster |
| 6,875,219 B2 | 4/2005 | Arramon et al. |
| 6,887,246 B2 | 5/2005 | Bhatnagar |
| 6,916,308 B2 | 7/2005 | Dixon et al. |
| 6,957,747 B2 | 10/2005 | Peeler et al. |
| 6,974,247 B2 | 12/2005 | Frei et al. |
| 6,974,416 B2 | 12/2005 | Booker et al. |
| 6,979,341 B2 | 12/2005 | Scribner et al. |
| 6,979,352 B2 | 12/2005 | Reynolds |
| 6,994,465 B2 | 2/2006 | Tague et al. |
| 6,997,930 B1 | 2/2006 | Jaggi |
| 7,008,433 B2 | 3/2006 | Voellmicke et al. |
| 7,025,771 B2 | 4/2006 | Kuslich et al. |
| 7,029,163 B2 | 4/2006 | Barker et al. |
| 7,044,954 B2 | 5/2006 | Reiley |
| 7,048,743 B2 | 5/2006 | Miller |
| 7,066,942 B2 | 6/2006 | Treace |
| 7,087,040 B2 | 8/2006 | McGuckin |
| 7,091,258 B2 | 8/2006 | Neubert et al. |
| 7,097,648 B1 | 8/2006 | Globerman et al. |
| 7,112,205 B2 | 9/2006 | Carrison |
| 7,116,121 B1 | 10/2006 | Holcombe et al. |
| 7,252,671 B2 | 8/2007 | Scribner |
| 7,264,622 B2 | 9/2007 | Michelson |
| 7,270,667 B2 | 9/2007 | Faccioli |
| 7,278,778 B2 | 10/2007 | Sand |
| 7,326,203 B2 | 2/2008 | Papineau et al. |
| 7,456,024 B2 | 11/2008 | Dahm et al. |
| 7,559,932 B2 | 7/2009 | Truckai et al. |
| 7,572,263 B2 | 8/2009 | Preissman |
| 7,575,577 B2 | 8/2009 | Boyd et al. |
| 7,604,618 B2 | 10/2009 | Dixon et al. |
| 7,666,205 B2 | 2/2010 | Weikel et al. |
| 7,678,116 B2 | 3/2010 | Truckai et al. |
| 7,717,918 B2 | 5/2010 | Truckai et al. |
| 7,722,620 B2 | 5/2010 | Truckai et al. |
| 8,038,682 B2 | 10/2011 | McGill et al. |
| 8,066,713 B2 | 11/2011 | DiMauro et al. |
| 8,070,753 B2 | 12/2011 | Truckai et al. |
| 8,360,629 B2 | 1/2013 | Globerman et al. |
| 8,361,078 B2 | 1/2013 | Beyar et al. |
| 8,415,407 B2 | 4/2013 | Beyar et al. |
| 8,540,722 B2 | 9/2013 | Beyar et al. |
| 8,809,418 B2 | 8/2014 | Beyar et al. |
| 8,950,929 B2 | 2/2015 | Globerman et al. |
| 8,956,368 B2 | 2/2015 | Beyar et al. |
| 9,186,194 B2 | 11/2015 | Ferreyro et al. |
| 9,259,696 B2 | 2/2016 | Globerman et al. |
| 2001/0012968 A1 | 8/2001 | Preissman |
| 2001/0024400 A1 | 9/2001 | Van Der Wel |
| 2001/0034527 A1 | 10/2001 | Scribner et al. |
| 2002/0008122 A1 | 1/2002 | Ritsche et al. |
| 2002/0010471 A1 | 1/2002 | Wironen |
| 2002/0010472 A1 | 1/2002 | Kuslich et al. |

(56) References Cited

U.S. PATENT DOCUMENTS

| | | |
|---|---|---|
| 2002/0013553 A1 | 1/2002 | Pajunk |
| 2002/0049448 A1 | 4/2002 | Sand et al. |
| 2002/0049449 A1 | 4/2002 | Bhatnagar et al. |
| 2002/0058947 A1 | 5/2002 | Hochschuler et al. |
| 2002/0067658 A1 | 6/2002 | Vendrely et al. |
| 2002/0068939 A1 | 6/2002 | Levy et al. |
| 2002/0068974 A1 | 6/2002 | Kuslich et al. |
| 2002/0068975 A1 | 6/2002 | Teitelbaum et al. |
| 2002/0072768 A1 | 6/2002 | Ginn |
| 2002/0082605 A1 | 6/2002 | Reiley et al. |
| 2002/0099384 A1 | 7/2002 | Scribner et al. |
| 2002/0099385 A1 | 7/2002 | Ralph et al. |
| 2002/0118595 A1 | 8/2002 | Miller |
| 2002/0156483 A1 | 10/2002 | Voellmicke et al. |
| 2002/0161373 A1 | 10/2002 | Osorio et al. |
| 2002/0177866 A1 | 11/2002 | Weikel et al. |
| 2002/0183851 A1 | 12/2002 | Spiegelberg et al. |
| 2002/0188300 A1 | 12/2002 | Arramon |
| 2002/0191487 A1 | 12/2002 | Sand |
| 2003/0009177 A1 | 1/2003 | Middleman et al. |
| 2003/0018339 A1 | 1/2003 | Higueras et al. |
| 2003/0031698 A1 | 2/2003 | Roeder et al. |
| 2003/0032929 A1 | 2/2003 | McGuckin et al. |
| 2003/0036763 A1 | 2/2003 | Bhatnagar et al. |
| 2003/0040718 A1 | 2/2003 | Kust et al. |
| 2003/0050644 A1 | 3/2003 | Boucher et al. |
| 2003/0050702 A1 | 3/2003 | Berger |
| 2003/0078589 A1 | 4/2003 | Preissman |
| 2003/0109883 A1 | 6/2003 | Matsuzaki et al. |
| 2003/0109884 A1 | 6/2003 | Tague et al. |
| 2003/0144742 A1 | 7/2003 | King et al. |
| 2003/0162864 A1 | 8/2003 | Pearson et al. |
| 2003/0174576 A1 | 9/2003 | Tague et al. |
| 2003/0181963 A1 | 9/2003 | Pellegrino et al. |
| 2003/0185093 A1 | 10/2003 | Vendrely et al. |
| 2003/0220414 A1 | 11/2003 | Axen et al. |
| 2003/0225364 A1 | 12/2003 | Kraft et al. |
| 2003/0227816 A1 | 12/2003 | Okamoto et al. |
| 2003/0231545 A1 | 12/2003 | Seaton |
| 2004/0010263 A1 | 1/2004 | Boucher et al. |
| 2004/0029996 A1 | 2/2004 | Kuhn |
| 2004/0054377 A1 | 3/2004 | Foster et al. |
| 2004/0059283 A1 | 3/2004 | Kirwan et al. |
| 2004/0066706 A1 | 4/2004 | Barker et al. |
| 2004/0068264 A1 | 4/2004 | Treace |
| 2004/0073139 A1 | 4/2004 | Hirsch et al. |
| 2004/0080357 A1 | 4/2004 | Chuang et al. |
| 2004/0092946 A1 | 5/2004 | Bagga et al. |
| 2004/0098015 A1 | 5/2004 | Weikel et al. |
| 2004/0106913 A1* | 6/2004 | Eidenschink et al. ......... 604/523 |
| 2004/0122438 A1 | 6/2004 | Abrams |
| 2004/0132859 A1 | 7/2004 | Puckett, Jr. et al. |
| 2004/0133124 A1 | 7/2004 | Bates et al. |
| 2004/0133211 A1 | 7/2004 | Raskin et al. |
| 2004/0138759 A1 | 7/2004 | Muller et al. |
| 2004/0157952 A1 | 8/2004 | Soffiati et al. |
| 2004/0157954 A1 | 8/2004 | Imai et al. |
| 2004/0162559 A1 | 8/2004 | Arramon et al. |
| 2004/0167532 A1 | 8/2004 | Olson et al. |
| 2004/0167562 A1 | 8/2004 | Osorio et al. |
| 2004/0167625 A1 | 8/2004 | Beyar et al. |
| 2004/0193171 A1 | 9/2004 | DiMauro |
| 2004/0215202 A1 | 10/2004 | Preissman |
| 2004/0220672 A1 | 11/2004 | Shadduck |
| 2004/0226479 A1 | 11/2004 | Lyles et al. |
| 2004/0229972 A1 | 11/2004 | Klee et al. |
| 2004/0230309 A1 | 11/2004 | DiMauro et al. |
| 2004/0236313 A1 | 11/2004 | Klein |
| 2004/0249015 A1 | 12/2004 | Jia et al. |
| 2004/0249347 A1 | 12/2004 | Miller et al. |
| 2004/0260303 A1 | 12/2004 | Carrison |
| 2004/0260304 A1 | 12/2004 | Faccioli et al. |
| 2004/0267154 A1 | 12/2004 | Sutton et al. |
| 2005/0014273 A1 | 1/2005 | Dahm et al. |
| 2005/0015148 A1 | 1/2005 | Jansen et al. |
| 2005/0025622 A1 | 2/2005 | Djeridane et al. |
| 2005/0058717 A1 | 3/2005 | Yetkinler |
| 2005/0060023 A1 | 3/2005 | Mitchell et al. |
| 2005/0070912 A1 | 3/2005 | Voellmicke |
| 2005/0070914 A1 | 3/2005 | Constantz et al. |
| 2005/0070915 A1 | 3/2005 | Mazzuca |
| 2005/0083782 A1 | 4/2005 | Gronau et al. |
| 2005/0113762 A1 | 5/2005 | Kay et al. |
| 2005/0143827 A1 | 6/2005 | Globerman et al. |
| 2005/0154081 A1 | 7/2005 | Yin et al. |
| 2005/0180806 A1 | 8/2005 | Green |
| 2005/0203206 A1 | 9/2005 | Trieu |
| 2005/0209695 A1 | 9/2005 | de Vries et al. |
| 2005/0216025 A1 | 9/2005 | Chern Lin et al. |
| 2005/0256220 A1 | 11/2005 | Lavergne et al. |
| 2005/0281132 A1 | 12/2005 | Armstrong et al. |
| 2006/0035997 A1 | 2/2006 | Orlowski et al. |
| 2006/0041033 A1 | 2/2006 | Bisig et al. |
| 2006/0052794 A1 | 3/2006 | McGill |
| 2006/0074433 A1 | 4/2006 | McGill et al. |
| 2006/0079905 A1 | 4/2006 | Beyar et al. |
| 2006/0116643 A1 | 6/2006 | Dixon et al. |
| 2006/0116689 A1 | 6/2006 | Albans et al. |
| 2006/0116690 A1 | 6/2006 | Pagano |
| 2006/0122614 A1 | 6/2006 | Truckai et al. |
| 2006/0148923 A1 | 7/2006 | Ashman et al. |
| 2006/0167148 A1 | 7/2006 | Engqvist et al. |
| 2006/0181959 A1 | 8/2006 | Weiss et al. |
| 2006/0235338 A1* | 10/2006 | Pacheco ......................... 600/587 |
| 2006/0241644 A1 | 10/2006 | Osorio et al. |
| 2006/0264695 A1 | 11/2006 | Viole et al. |
| 2006/0264967 A1 | 11/2006 | Ferreyro et al. |
| 2006/0266372 A1 | 11/2006 | Miller et al. |
| 2006/0271061 A1* | 11/2006 | Beyar et al. .................... 606/105 |
| 2006/0276819 A1 | 12/2006 | Osorio et al. |
| 2007/0027230 A1 | 2/2007 | Beyar et al. |
| 2007/0032567 A1 | 2/2007 | Beyar et al. |
| 2007/0055266 A1 | 3/2007 | Osorio et al. |
| 2007/0055267 A1 | 3/2007 | Osorio et al. |
| 2007/0055278 A1 | 3/2007 | Osorio et al. |
| 2007/0055280 A1 | 3/2007 | Osorio et al. |
| 2007/0055284 A1 | 3/2007 | Osorio et al. |
| 2007/0055285 A1 | 3/2007 | Osorio |
| 2007/0055300 A1 | 3/2007 | Osorio et al. |
| 2007/0060941 A1 | 3/2007 | Reiley et al. |
| 2007/0118142 A1 | 5/2007 | Krueger |
| 2007/0142842 A1 | 6/2007 | Krueger |
| 2007/0197935 A1 | 8/2007 | Reiley et al. |
| 2007/0198013 A1 | 8/2007 | Foley et al. |
| 2007/0198023 A1 | 8/2007 | Sand et al. |
| 2007/0198024 A1 | 8/2007 | Plishka et al. |
| 2007/0255282 A1 | 11/2007 | Simonton et al. |
| 2007/0282443 A1 | 12/2007 | Globerman et al. |
| 2008/0039856 A1 | 2/2008 | DiMauro |
| 2008/0044374 A1 | 2/2008 | Lavergne et al. |
| 2008/0058827 A1 | 3/2008 | Osorio et al. |
| 2008/0065087 A1 | 3/2008 | Osorio et al. |
| 2008/0065089 A1 | 3/2008 | Osorio et al. |
| 2008/0065137 A1 | 3/2008 | Boucher et al. |
| 2008/0065142 A1 | 3/2008 | Reiley et al. |
| 2008/0065190 A1 | 3/2008 | Osorio et al. |
| 2008/0071283 A1 | 3/2008 | Osorio et al. |
| 2008/0086133 A1 | 4/2008 | Kuslich et al. |
| 2008/0132935 A1 | 6/2008 | Osorio et al. |
| 2008/0140079 A1 | 6/2008 | Osorio et al. |
| 2008/0140084 A1 | 6/2008 | Osorio et al. |
| 2008/0212405 A1 | 9/2008 | Globerman et al. |
| 2008/0228192 A1 | 9/2008 | Beyar et al. |
| 2009/0264892 A1 | 10/2009 | Beyar et al. |
| 2009/0264942 A1 | 10/2009 | Beyar et al. |
| 2009/0270872 A1 | 10/2009 | DiMauro |
| 2010/0065154 A1 | 3/2010 | Globerman |
| 2010/0069786 A1 | 3/2010 | Globerman |
| 2010/0152855 A1 | 6/2010 | Kuslich et al. |
| 2010/0168271 A1 | 7/2010 | Beyar |
| 2010/0268231 A1 | 10/2010 | Kuslich et al. |
| 2012/0307586 A1 | 12/2012 | Globerman et al. |
| 2013/0123791 A1 | 5/2013 | Beyar et al. |
| 2013/0261217 A1 | 10/2013 | Beyar et al. |

(56) References Cited

U.S. PATENT DOCUMENTS

| | | | |
|---|---|---|---|
| 2013/0345708 A1 | 12/2013 | Beyar et al. | |
| 2014/0088605 A1 | 3/2014 | Ferreyro et al. | |
| 2014/0148866 A1 | 5/2014 | Globerman et al. | |
| 2015/0122691 A1 | 5/2015 | Globerman et al. | |
| 2015/0127058 A1 | 5/2015 | Beyar et al. | |
| 2015/0148777 A1 | 5/2015 | Ferreyro et al. | |

FOREIGN PATENT DOCUMENTS

| | | |
|---|---|---|
| CN | 1138001 A | 12/1996 |
| CN | 1310026 A | 8/2001 |
| DE | 136018 C | 11/1902 |
| DE | 226956 | 3/1909 |
| DE | 868497 C | 2/1953 |
| DE | 1283448 | 11/1968 |
| DE | 1810799 | 6/1970 |
| DE | 2821785 | 11/1979 |
| DE | 3003947 | 8/1980 |
| DE | 2947875 | 4/1981 |
| DE | 3443167 | 6/1986 |
| DE | 8716073 | 3/1988 |
| DE | 3817101 A1 | 11/1989 |
| DE | 3730298 | 2/1990 |
| DE | 4104092 | 8/1991 |
| DE | 293485 | 9/1991 |
| DE | 4016135 | 3/1992 |
| DE | 4315757 | 11/1994 |
| DE | 19612276 | 10/1997 |
| DE | 10258140 | 7/2004 |
| EP | 20207 | 6/1908 |
| EP | 486638 | 6/1938 |
| EP | 0044877 | 2/1982 |
| EP | 0190504 | 3/1986 |
| EP | 0177781 | 4/1986 |
| EP | 0235905 | 9/1987 |
| EP | 0301759 | 7/1988 |
| EP | 0242672 | 9/1989 |
| EP | 0425200 | 10/1990 |
| EP | 0423916 | 4/1991 |
| EP | 0475077 | 3/1992 |
| EP | 0511868 | 4/1992 |
| EP | 0493789 | 7/1992 |
| EP | 0581387 | 2/1994 |
| EP | 0 614 653 A2 | 9/1994 |
| EP | 0669100 | 8/1995 |
| EP | 0748615 | 12/1996 |
| EP | 0763348 | 3/1997 |
| EP | 1074231 | 2/2001 |
| EP | 1095667 | 5/2001 |
| EP | 1103237 | 5/2001 |
| EP | 1104260 | 6/2001 |
| EP | 1 247 454 A1 | 10/2002 |
| EP | 1464292 | 10/2004 |
| EP | 1148850 | 4/2005 |
| EP | 1552797 | 7/2005 |
| EP | 1570873 | 9/2005 |
| EP | 1598 015 | 11/2005 |
| EP | 1148851 | 5/2006 |
| EP | 1 829 518 A1 | 9/2007 |
| EP | 1 886 647 A1 | 2/2008 |
| FR | 1548575 | 10/1968 |
| FR | 2606282 | 5/1988 |
| FR | 2629337 | 10/1989 |
| FR | 2638972 | 5/1990 |
| FR | 2674119 | 9/1992 |
| FR | 2690332 | 10/1993 |
| FR | 2712486 | 5/1995 |
| FR | 2722679 | 1/1996 |
| GB | 8331 | 0/1904 |
| GB | 179502045 | 4/1795 |
| GB | 190720207 A | 6/1908 |
| GB | 408668 | 4/1934 |
| GB | 486638 A | 6/1938 |
| GB | 2114005 | 8/1983 |
| GB | 2156824 | 10/1985 |
| GB | 2197691 | 5/1988 |
| GB | 2268068 | 1/1994 |
| GB | 2276560 | 10/1994 |
| GB | 2411849 | 9/2005 |
| GB | 2413280 | 10/2005 |
| GB | 2469749 | 10/2010 |
| JP | 51-134465 A | 11/1976 |
| JP | 54-009110 | 1/1979 |
| JP | 55-009242 U | 1/1980 |
| JP | 55-109440 | 8/1980 |
| JP | 62-068893 | 3/1987 |
| JP | 63-194722 A | 8/1988 |
| JP | 02-122017 | 5/1990 |
| JP | 02-166235 | 6/1990 |
| JP | 02-125730 U | 10/1990 |
| JP | 04-329956 A | 11/1992 |
| JP | 07-000410 | 1/1995 |
| JP | 8322848 | 12/1996 |
| JP | 10146559 | 6/1998 |
| JP | 10-511569 | 10/1998 |
| JP | 2001-514922 A | 9/2001 |
| JP | 2004-16707 | 1/2004 |
| JP | 2005-500103 A | 1/2005 |
| JP | 2008-55367 | 3/2008 |
| RO | 116784 | 6/2001 |
| RU | 662082 | 5/1979 |
| RU | 1011119 | 4/1983 |
| RU | 1049050 | 10/1983 |
| WO | WO 90/00037 | 1/1990 |
| WO | WO 92/14423 | 9/1992 |
| WO | WO 94/12112 | 6/1994 |
| WO | WO 95/13862 | 5/1995 |
| WO | WO 96/11643 | 4/1996 |
| WO | WO 96/19940 | 7/1996 |
| WO | WO 96/32899 | 10/1996 |
| WO | WO 96/37170 | 11/1996 |
| WO | WO 97/18769 | 5/1997 |
| WO | WO 97/28835 | 8/1997 |
| WO | WO 98/28035 | 7/1998 |
| WO | WO 98/38918 | 9/1998 |
| WO | WO 99/18866 | 4/1999 |
| WO | WO 99/18894 | 4/1999 |
| WO | WO 99/29253 | 6/1999 |
| WO | WO 99/37212 | 7/1999 |
| WO | WO 99/39661 | 8/1999 |
| WO | WO 99/49819 | 10/1999 |
| WO | WO 99/52446 | 10/1999 |
| WO | WO 00/06216 | 2/2000 |
| WO | WO 00/44319 | 8/2000 |
| WO | WO 00/44321 | 8/2000 |
| WO | WO 00/44946 | 8/2000 |
| WO | WO 00/54705 | 9/2000 |
| WO | WO 00/56254 | 9/2000 |
| WO | WO 01/08571 | 2/2001 |
| WO | WO 01/13822 | 3/2001 |
| WO | WO 01/54598 | 8/2001 |
| WO | WO 01/60270 | 8/2001 |
| WO | WO 01/76514 | 10/2001 |
| WO | WO 02/00143 | 1/2002 |
| WO | WO 02/02033 | 1/2002 |
| WO | WO 02/19933 | 3/2002 |
| WO | WO 02/064062 | 8/2002 |
| WO | WO 02/064194 | 8/2002 |
| WO | WO 02/072156 | 9/2002 |
| WO | WO 02/096474 | 12/2002 |
| WO | WO 03/007854 | 1/2003 |
| WO | WO 03/015845 | 2/2003 |
| WO | WO 03/022165 | 3/2003 |
| WO | WO 03/061495 | 7/2003 |
| WO | WO 03/078041 | 9/2003 |
| WO | WO 03/101596 | 12/2003 |
| WO | WO 2004/002375 | 1/2004 |
| WO | WO 2004/019810 | 3/2004 |
| WO | WO 2004/071543 | 8/2004 |
| WO | WO 2004/075965 | 9/2004 |
| WO | WO 2004/080357 | 9/2004 |
| WO | WO 2004/110292 | 12/2004 |
| WO | WO 2004/110300 | 12/2004 |

(56) References Cited

FOREIGN PATENT DOCUMENTS

| | | |
|---|---|---|
| WO | WO 2005/000138 | 1/2005 |
| WO | 2005/017000 A1 | 2/2005 |
| WO | WO 2005/032326 | 4/2005 |
| WO | WO 2005/048867 | 6/2005 |
| WO | WO 2005/051212 | 6/2005 |
| WO | WO 2005/110259 | 11/2005 |
| WO | WO 2006/011152 | 2/2006 |
| WO | WO 2005/032326 | 4/2006 |
| WO | WO 2006/039159 | 4/2006 |
| WO | 2006/062939 A2 | 6/2006 |
| WO | WO 2006/090379 | 8/2006 |
| WO | WO 2007/015202 | 2/2007 |
| WO | WO 2007/036815 | 4/2007 |
| WO | WO 2007/148336 | 12/2007 |
| WO | WO 2008/004229 | 1/2008 |
| WO | WO 2008/032322 | 3/2008 |
| WO | WO 2008/047371 | 4/2008 |

OTHER PUBLICATIONS

Heini et al. "The Use of a Side-Opening Injection Cannula in Vertebroplasty", Spine, 27(1): 105-109, 2002.
Hernandez et al. "Influence of Powder Particle Size Distribution on complex Viscosity and other Properties of Acrylic Bone Cement for Vetebroplasty and Kyphoplasty", Journal of Biomed. Material Research, Part. B, 77B: 98-103, 2006.
Ishikawa et al. "Effects of Neutral Sodium Hydrogen Phosphate on Setting Reaction and Mechanical Strength of Hydroxyapatite Putty", Journal of Biomedical Meterials Research, 44: 322-329, 199.
Ishikawa et al. "Non-Decay Type Fast-Setting Calcium Phosphate Cement: Hydroxyapatite Putty Containing an Increased Amount of Sodium Alginate", Journal of Biomed. Materials Research, 36: 393-399, 1997.
Krause et al. "The Viscosity of Acrylic Bone Cements", Jouirnal of Biomedical Materials Research, 16: 219-243, 1982.
Nussbaum et al. "The Chemistry of Acrylic Bone Cements and Implications for Clinical Use in Image-Guided Therapy", Journal of Vasc. Interv. Radiol., 15: 121-126, 2004.
Weissman et al. "Trochanteric Fractures of the Femur. Treatment With a Strong Nail and Early Weight-Bearing", Clinical Orthopedics and Related Research, 67: 143-150, 1969. Fig.
Canale et al. "Campbell's Operative Orthopaedics—vol. three— Ninth edition", Mosby: p. 2097,2121, 2184-2185, 2890-2896, 1998. Abstract.
Cole et al. "AIM Titanium Humeral Nail System", Sugical Technique, DePuy Orthopedics, 17 P., 2000.
Edeland "Some Additional Suggestions for an Intervertebral Disc Prothesis", Journal of Biomedical Engineering, XP008072822, 7(1): 57-62, Jan. 1985. Figs.3a-3d.
Steen "Laser Surface Treatment", Laser Material Processing, Springer, 2nd Ed., Chap.6: 218-271, 2003.
Varela et al. "Closed Intramedullary Pinning of Metacarpal and Phalanx Fractures", Orthopedics, 13(2): 213-215, 1990. Abstract.
Al-Assir, et al., "Percutaneous Vertebroplasty: A Special Syringe for Cement Injection," AJNR Am. J. Neuroradiol. 21:159-61 (Jan. 2000).
Amar, Arun P. et al., "Percutaneous Transpedicular Polymethylmethacrylate Vertebroplasty for the Treatment of Spinal Compression Fractures," Neurosurgery 49(5):1105-15 (2001).
Andersen, M. et al., "Vertebroplastik, ny behandling of osteoporotiske columnafrakturer?", Ugeskr Laefer 166/6:463-66 (Feb. 2, 2004).
Avalione & Baumeister III, Marks' Standard Handbook for Mechanical Engineers, 10 ed, pp. 5-6 (1996).
Barr, J.D., "Percutaneous Vertebroplasty for pain Relief and Spinal Stabilization," Spine 25(8):923-28 (2000).
Belkoff, S. et al., The Biomechanics of Vertebroplasty, the Effect of Cement Volume on Mechanical Behavior, SPINE 26(14):1537-41 (2001).
Belkoff, S.M. et al., "An Ex Vivo Biomechanical Evaluation of a Hydroxyapatite Cement for Use with Kyphoplasty," Am. J. Neurorad. 22:1212-16 (2001).
Belkoff, S.M. et al., "An Ex Vivo Biomechanical Evaluation of a Inflatable Bone Tamp Used in the Treatment of Compression Fracture," SPINE 26(2):151-56 (2001).
Belkoff, S.M. et al., "An In Vitro Biomechanical Evaluation of Bone Cements Used in Percutaneous Vertebroplasty, " Bone 25(2):23S-26S (1999).
Blinc, A et al., "Methyl-methacrylate bone cement surface does not promote platelet aggregation or plasma coagulation in vitro," Thrombosis Research 114:179-84 (2004).
Bohner, M. et al., "Theoretical and Experimental Model to Describe the Injection of a Polymethacrylate Cement into a Porous Structure," Biomaterials 24(16):2721-30 (2003).
Breusch, S. et al., "Knochenzemente auf Basis von Polymethylmethacrylat," Orthopade 32:41-50 (2003) w/ abs.
Carrodegus et al., "Injectable Acrylic Bone Cements for Vertebroplasty with Improved Properties," J. Biomed. Materials Res. 68(1):94-104 (Jan. 2004).
Codman & Shurtleff, "V-MAX™ Mixing and Delivery Device," Catalog No. 43-1056.
Combs, S. et al., "The Effects of Barium Sulfate on the Polymerization Temperature and Shear Strength of Surgical Simplex P," Clin. Ortho. and Related Res. pp. 287-291 (Jun. 4, 1979).
Cotton, A. et al., "Percutaneous Vertebroplasty: State of the Art," Scientific Exhibit, Radiographics 18:311-20 (1998).
Dean, J.R. et al., "The Strengthening Effect of Percutaneous Vertebroplasty," Clin Radiol. 55:471-76 (2000).
Deramond, H. et al, "Percutaneous Vertebroplasty with Polymethylmethacrylate, Technique Indications and Results," Radiologic Clinics of North America 36(3) (May 1988).
Deramond, H. et al., "Temperature Elevation Caused by Bone cement Polymerization During Vertbroplasty," Bone 25(2):17S-21S (1999).
DeWijn, J.R., Characterization of Bone Cements, The Institute of Dental Materials Science and Technology and the Dept of Ortho., Catholic University, Netherlands 46:38-51 (1975).
European Search Report, from EP05763930.4; mailed Sep. 11, 2008.
European Search Report, from EP09151379.6, mailed Oct. 20, 2009.
European Search Report, from EP06780252.0, mailed Oct. 29, 2009.
Farrar, D.F. et al., "Rheological Properties of PMMA Bone Cements During Curing," Biomaterials 22:3005-13 (2001).
Fessler, Richard D. et al., "Vertebroplasty," Neurosurgical Operative Atlas 9:233-240 (2000).
Gangi, A., "CT-Guided Interventional Procedures for Pain Management in the Lumbosacral Spine," Radiographics 18:621-33 (1998).
Gangi, A., "Computed Tomography CT and Fluoroscopy-Guided Vertebroplasty: Results and Complications in 187 Patients," Seminars in Interventional Radiology 16(2):137-42 (1999).
Gangi, A., "Percutaneous Vertebroplasty Guided by a Combination of CT and Fluoroscopy," AJNR 15:83-86 (1994).
Garfin, S. R. et al., "New Technologies in Spine, Kyphoplasty and Vertebroplasty for the Treatment of Painful Osteoporotic Compression Fractures," Spine 26(14:1511-15 (2001).
Gheduzzi, S. et al., "Mechanical Characterisation of Three Percutaneous Vertebroplasty Biomaterials," J. Mater Sci Mater Med 17(5):421-26 (2006).
Giannitsios, D. et al., "High Cement Viscosity Reduces Leakage Risk in Vertebroplasty," European Cells & Mat. 10 supp. 3:54 (2005).
Grados F. et al.,"Long-Term Observations of Vertebral Osteoporotic Fractures Treated by Percutaneous Vertebroplasty," Rheumatology 39:1410-14 (2000).
Hasenwinkel, J. et al., "A Novel High-Viscosity, Two-Solution Acrylic Bone Cement: Effect of Chemical Composition on Properties," J. Biomed. Materials Research 47(1):36-45 (1999).
Hasenwinkel, J. et al., "Effect of Initiation Chemistry on the Fracture Toughness, Fatigue Strength, and Residual Monomer Content of a Novel High-Viscosity, Two-Solution Acrylic Bone Cement," J. Biomed. Materials Res. 59(3):411-21 (2001).
Heini, P. et al., "Augmentation of Mechanical Properties in Osteoporatic Vertebral Bones—a Biomechanical Investigation of Vertebroplasty Efficacy With Different Bone Cements," EUR Spine J. v. 10, pp. 164-171, Springer-Verlag (2001).
Heini, P., "Percutaneous Transpedicular Vertebroplasty with PMMA: Operative Technique and Early Results," EUR Spine J. v. 9, pp. 445-450, Springer-Verlag (2000).

(56) References Cited

OTHER PUBLICATIONS

Heraeus Palacos R, 2008, Palacos R, high Viscosity Bone Cement.
International Preliminary Report on Patentability, from PCT/IB06/053014, dated Apr. 10, 2008.
International Search Report, from PCT/IL06/00239, mailed Jan. 26, 2007.
International Search Report, from PCT/IL05/00812, mailed Feb. 28, 2007.
International Search Report, from PCT/IB06/052612, mailed Oct. 2, 2007.
International Search Report, from PCT/IL07,00833, mailed Apr. 4, 2008.
International Search Report, from PCT/IL07/00484, mailed Apr. 17, 2008.
International Search Report, for PCT/MX03/000027, filed Mar. 14, 2003.
Jasper, L.E. et al., "The Effect of Monomer-to-Powder Ratio on the Material Properties of Cranioplastic," Bone 25(2):27S-29S (1999).
Jensen, Mary E. et al., "Percutaneous Polymethylmethacrylate Vertebroplasty in the Treatment of Osteoporotic Vertebral Body Compression Fractures: Technical Aspects," AJNR 18:1897-1904 (1997).
Jensen, Mary E. et al., "Percutaneous Vertebroplasty in the Treatment of Osteoporotic Compression Fractures," Spine Interventions 10(3):547-568 (2000).
Johnson & Johnson Orthopaedics, The CEMVAC Method, Raynham, MA.
Kallmes, D. et al., "Radiation Dose to the Operator During Vertebroplasty: Prospective Comparison of the Use of 1-cc Syringes Versus an Injection Device," AJNR Am. J. Neuroradiol. 24:1257-60 (2003).
Kaufmann et al, "Age of Fracture and Clinical Outcomes of Percutaneous Vertebroplasty," Am. J. Neuroradiology 22:1860-63 (2001).
Kuhn, Klaus-Dieter, Bone Cements—Uptodate Comparison of Physical and Chemical Properties of Commercial Materials, Springer-Verlag Heidelberg Germany p. 7-8, 17, 38 (2000).
Kyphom Medical Professionals, KyphXProducts (Nov. 8, 2001).
Lewis, "Properties of Acrylic Bone Cement: State of the Art Review," J. Biomed. Mat. Res. Appl. Biomaterials 38(2):155-82 (p. 158 s.Viscosity) (1997).
Lewis, G. et al., "Rheological Properties of Acrylic Bone Cement During Curing and the Role of the Size of the Powder Particles," J. Biomed. Mat. Res. Appl. Biomat. 63(2):191-99 (2002).
Lewis, "Toward Standardization of Methods of Determination of Fracture Properties of Acrylic Bone Cement and Statistical Analysis of Test Results," J. Biomed. Research: Appl. Biomaterials 53(6):748-68 (2000).
Li, C. et al., "Thermal Characterization of PMMA-Based Bone Cement Curing," J. Materials Sci.: Materials in Medicine 15:84-89 (2004).
Lieberman, I.H. et al., "Initial Outcome and Efficacy of Kyphoplasty in the Treatment of Painful Osteoporatic Vertebral Compression Fractures," Spine 26(14:1631-38 (2001).
Mathis, John et al., "Percutaneous Vertebroplasty: A Developing Standard of Care for Vertebral Compression Fractures," AJNR Ann. J. Neurorad. 22:373-81 (2001).
Medsafe Palacos R 2007, Data Sheet : Palacos R Bone cement with Garamycin pp. 1-7; http://www.medsafe.govt.nz/profs/datasheet/p/palacosbonecements.htm.
Mousa, W.F. et al., "Biological and Mechanical Properties of PMMA-Based Bioactive Bone Cements," Biomaterials 21:2137-46 (2000).
O'Brien, J. et al., "Vertebroplasty in patients with Severe Vertebral Compression Fractures: A Technical Report," AJNR 21:1555-58 (2000).
Odian, G., "Principles of Polymerization," pp. 20-23.
Padovani, B. et al., "Pulmonary Embolism Caused by Acrylic Cement: A Rare Complication of Percutaneous Vertebroplasty," AJNR 20:375-77 (1999).
Parallax Medical, Inc., Exflow Cement Delivery System (May 16, 2000).
Pascual, B. et al., "New Aspects of the Effect of Size and Size Distribution on the Setting Parameters and Mechanical Properties of Acrylic Bone Cements," Biomaterials 17(5):509-16 (1996).
Rimnac, CM, et al., "The effect of centrifugation on the fracture properties of acrylic bone cements," JB&JS 68A(2):281-87 (1986).
Robinson, R. et al., "Mechanical Properties of Poly(methyl methacrylate) Bone Cement," J. Biomed. Materials Res. 15(2):203-08 (2004).
Ryu, K. S. et al., "Dose-Dependent Epidural Leakage of Polymethylmethacrylate after Percutaneous Vertebroplasty in Patients with Osteoporotic Vertebral Compression Fractures," J. Neuro: Spine 96:56-61 (2002).
Saha, S. et a., "Mechanical Properties of Bone Cement: A Review," J. Biomed. Materials Res. 18(4):435-62 (1984).
Serbetci, K. et al., "Thermal and Mechanical Properties of Hydroxyapatite Impregnated Acrylic Bone Cements," Polymer Testing 23:145-55 (2004).
Shah, T., Radiopaque Polymer Formulations for Medical Devices; Medical Plastics and Biomaterials Special Section; Medical device & Diagnostic Industry pp. 102-111 (2000).
Supp. EP Search Report, from EP Appl. No. 05763930.4, dated Sep. 11, 2008.
Supp. EP Search Report, from EP Appl. No. 06711221.9, dated Sep. 15, 2008.
Vasconcelos, C., "Transient Arterial Hypotension Induced by Polymethyacrylated Injection During Percutaneous Vertebroplasty," Letter to the Editor, JVIR (Aug. 2001).
Wimhurst, J.A., et al., "The Effects of Particulate Bone Cements at the Bone-Implant Interface," J. Bone & Joint Surgery pp. 588-592 (2001).
Wimhurst, J.A. et al., "Inflammatory Responses of Human Primary Macrophages to Particulate Bone Cements in Vitro," J. Bone & Joint Surgery 83B:278-82 (2001).
Zapalowicz, K. et al., "Percutaneous Vertebroplasty with Bone Cement in the Treatment of Osteoporotic Vertebral Compression Fractures," Ortopedia Traumatologia Rehabilitacja NR Jan. 2003.
JP Office Action, from JP Appl No. 2009-517607, mailed Aug. 9, 2011.
Baroud, G., "Influence of Mixing Method on the Cement Temperature-Mixing Time History and Doughing Time of Three Acrylic Cements for Vertebroplasty," Wiley Periodicals Inc. 112-116 (2003).
European Search Report, from EP 10182769.9, mailed Mar. 2, 2011.
European Search Report, from EP 10182693.1, mailed Mar. 2, 2011.
European Search Report, from EP 10192302.7, mailed Mar. 24, 2011.
European Search Report, from EP 10192301.9, mailed Mar. 24, 2011.
European Search Report, from EP 10192300.1, mailed Mar. 24, 2011.
Feldman, H., "Die Geschichte der Injektionen," Laryngo-Rhino-Othol 79:239-46 (2000).
Glasgow Medico-Chirurgical Society, The lancet 1364 (May 18, 1907).
Greenberg, "Filling Root Canals by an Injection Technique," Dental Digest 61-63 (Feb. 1963).
Greenberg, "Filling Root Canals in Deciduous Teeth by an Injection Technique," Dental Digest 574-575 (Dec. 1961).
Greig, D., "A New Syringe for Injecting Paraffin," The Lancet 611-12 (Aug. 29, 1903).
Hide, I. et al., "Percutaneous Vertebroplasty: History, Technique and current Perspectives," Clin. Radiology 59:461-67 (2004).
Hu, M. et al., "Kyphoplasty for Vertebral Compression Fracture Via a Uni-Pedicular Approach," Pain Phys. 8:363-67 (2005).
International Search Report, from corresponding PCT/IL07/01257, dated Jul. 15, 2008.
Lake, R., "The Restoration of the Inferior Turbinate Body by Paraffin Injections in the Treatment of Atrophic Rhinitis," The Lancet 168-69 (Jan. 17, 1903).
Liang, B. et al., "Preliminary Clinical Application of Percutaneous Vertebroplasty," Zhong Nan Da Xue Bao Yi Xue Ban 31(1):114-9 (2006)(abs. only).

(56) References Cited

OTHER PUBLICATIONS

Noetzel, J. et al., Calcium Phosphate Cements in Medicine and Denistry—A Review of Literature, Schweiz Monatsschr Zehmed 115(12):1148-56 (2005)(abs. only).
Paget, S., "The Uses of Paraffin in Plastic Surgery," The Lancet 1354 (May 16, 1903).
Supp. EP Search Report, from EP Appl. No. 07766863.0, dated Apr. 12, 2011.
Walton, A, "Some Cases of Bone Cavities Treated by Stopping With Paraffin," The Lancet 155 (Jan. 18, 1908).
International Search Report, for PCT/IL07/00808, issued Aug. 22, 2008.
Marks, Standard handbook for mechanical engineers, section 5 (Tenth ed. 1996).
Supp. EP Search Report, from EP 07766838.2, dated May 18, 2011.
Cromer, A., "Fluids," Physics for the Life Sciences, 2:136-37 (1977).
JP Office Action, from JP Appl No. 2008-532910, mailed Jul. 19, 2011.
Lindeburg, M., "External Pressurized Liquids," Mechanical Eng. Ref. Manual for the PE Exam, 10:15-14(May 1997).
[No Author Listed] Simplex P Bone Cement. Stryker Corporation, 2 pages, publication date unknown. Retrieved from <http://www.stryker.com/en-us/products/Orthopaedics/BoneCementSubstitutestindex.htm>.
[No Author Listed] Standard Specification for Acrylic Bone Cement Designation F 451-08, ASTM International (2008), 11 pages.
Australian Office Action issued Mar. 7, 2013 for Application No. 2012203300 (6 pages).
Chinese Office Action for Application No. 201310064546.9, issued Jul. 31, 2014 (24 pages).
European Search Report, from EP07827231.7, mailed Sep. 12, 2011 (9 pages).
European Communication Issued Jul. 1, 2015 for Application No. 10182769.9, enclosing third party observations aonceming patentability (Submission dated Jun. 25, 2015) (6 pages).
European Communication for Application No. 10192301.9, issued Sep. 17, 2015, enclosing third party observations concerning patentability (Submission dated Sep. 11, 2015 (22 pages).
European Search Report for Application No. 12181745.6, issued Sep. 25, 2012. (9 pages).
European Search Report for Application No. 13174874.1, issued Nov. 13, 2013 (6 pages).
Extended European Search Report for Application No. 14166420.1, issued Jul. 14, 2014 (9 pages).
Japanese Office Action issued Apr. 9, 2013 for Application No. 2007-556708.
Japanese Office Action issued Dec. 6, 2011 for Application No. 2008-524651 (9 Pages).
Japanese Office Action for Application No. 2009-516062, dated Oct. 16, 2012 (6 pages).
Japanese Interrogation for Application No. 2009-516062 issued Jul. 9, 2013 (9 Pages).
Japanese Office Action for Application No. 2009-517607, dated Aug. 28, 2012. (4 pages).
Japanese Office Action for Application No. 2009-517607, dated Aug. 27, 2013. (6 pages).
Japanese Office Action for Application No. 2009-517607, dated Feb. 4, 2014. (8 pages).
Juneja, BL, Plastic Deformation of Metals and Related Properties. Chapter 1. New Age International. P1-29, 2010.
Kuehn et al., Acrylic bone cements: composition and properties. Orthop Clin North Am. Jan. 2005; 36(1):17-28, v.
Lu Orthopedic Bone Cement. Biomechanics and Biomaterials in Orthopedics. Ed. Poitout London: Springer-Verlag London Limited Jul. 2004 86-88.
Mendizabal et al., Modeling of the curing kinetics of an acrylic bone cement modified with hydroxyapatite. International Journal of Polymeric Materials. 2003;52:927-938.
Morejon et al., Kinetic effect of hydroxyapatite types on the polymerization of acrylic bone cements. International Journal of Polymeric Materials. 2003 ;52(7):637-654.
Sreeja et al., Studies on poly(methyl methacrylate)/polystyrene copolymers for potential bone cement applications. Metals Materials and Processes 1996; 8(4):315-322.
Su, W.-F, Polymer Size and Polymer Solutions. Principles of Polymer Design and Synthesis. Chapter 2, pp. 9-26, Springer-Verlag Berlin Heidelberg, 2013.
Yang et al., Polymerization of acrylic bone cement investigated by differential scanning calorimetry: Effects of heating rate and TCP content Polymer Engineering and Science. Jul. 1997;1182-1187.

\* cited by examiner

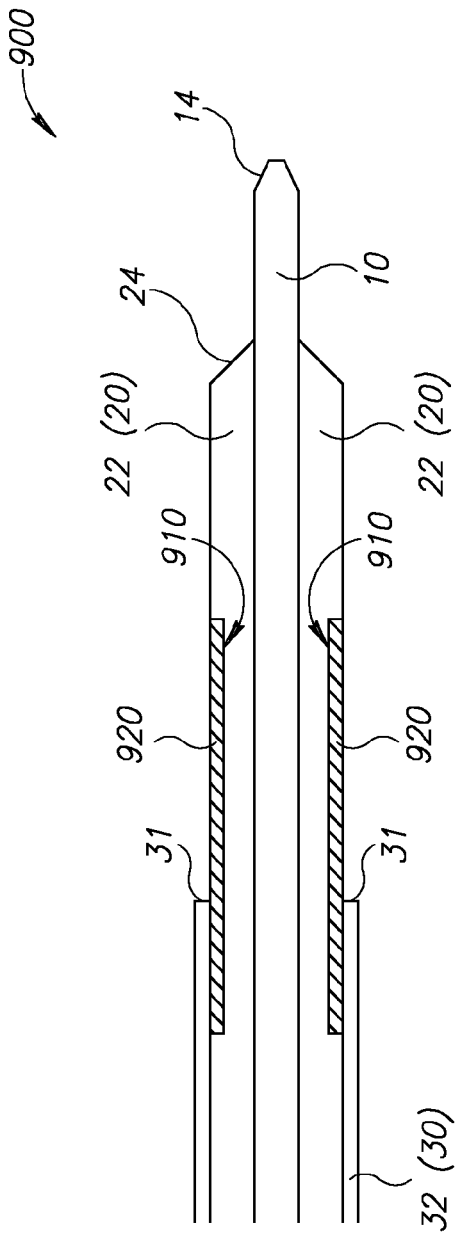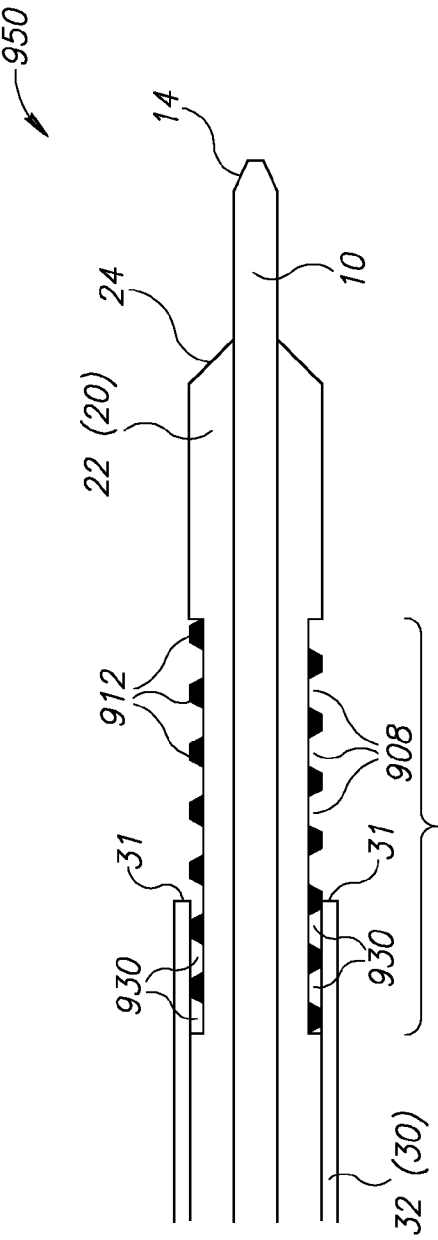

MARKED TOOLS

RELATED APPLICATIONS

This application claims the benefit under 35 U.S.C. §119 (e) of U.S. provisional patent application 60/720,725 filed Sep. 28, 2005 and entitled "Tools and Methods for Treating Bones" the disclosure of which is fully incorporated herein by reference.

This application is a continuation in part of PCT application IL2005/000812 filed Jul. 31, 2005, published as WO 2006/011152 and entitled "Materials, Devices and Methods for Treating Bones and Other Tissues" and of U.S. patent application Ser. No. 11/194,411 filed Aug. 1, 2005 and entitled "Materials, Devices and Methods for Treating Bones and Other Tissues" the disclosures of which are fully incorporated herein by reference.

This application is related to U.S. provisional patent application 60/646,539 filed Jan. 25, 2005 and entitled "Tools and Methods for Treating Bones" the disclosure of which is fully incorporated herein by reference.

FIELD OF INVENTION

The present invention relates to surgical tools characterized by markings which are visible under X-ray.

BACKGROUND OF THE INVENTION

Surgical treatment of fractured bones, osteoporotic bones, deformed bones and the like usually requires gaining an access into the interior of the bone as a first stage. When minimally invasive surgery is involved, such as percutaneous surgery, the step of accessing the bone is limited by dimensional requirements. The preferred tool should have minimal diameter and should provide safe and minimally invasive access into the bone in an uncomplicated manner.

Fixation of vertebral body fractures, for instance, may comprise fracture reduction and/or creation of a void in the cancellous bone, followed by injection of bone void filler/bone cement (PMMA), in order to reinforce the vertebral body. Exemplary fixation of this type is described in PCT/IL2004/000527; and U.S. Pat. Nos. 4,969,888 and 5,108,404 which are each fully incorporated herein by reference. The standard procedure includes gaining an access into the vertebral body optionally through the pedicle, using a needle and stylet assembly (such as Jamshidi needle), having a diameter of about 2.5-3.5 mm. The inner stylet is removed and replaced with a guide wire of about 1.5 mm diameter. Then, a small incision is made in the skin, and a trocar with a cone-shaped distal end is introduced over the guide wire, to enable passage through soft tissue. A cannula of about 4-6 mm diameter is introduced over the trocar, up to the pedicle, and the trocar is removed. Optionally, the trocar and cannula are assembled and introduced together. At this stage, a cannulated 3-6 mm diameter drill/reamer is advanced over the guide wire and via the cannula to enlarge the passage into the vertebral body. Optionally, the trocar and the drill are combined to one reamer. Normally, a manually operated drill/reamer is used. The guide wire and drill/reamer are removed, leaving the cannula inside the body. The rest of the procedure may proceed through the cannula. As can be seen, accessing the bone is a multiple-stage procedure, which is time consuming.

Lately a more shortened procedure is being used, during which a larger diameter Jamshidi needle is firstly introduced into the vertebral body. Following insertion, the stylet is withdrawn and the drilling stage and the rest of operation proceed via the needle, which serves as a working sleeve. Typically, positioning the Jamshidi needle into the pedicle may require several insertions (e.g., trial and error attempts) into the pedicle.

SUMMARY OF THE INVENTION

An aspect of some embodiments of the invention relates to detecting a less visible tool portion positioned adjacent a more visible tool portion when using X-ray based imaging. In an exemplary embodiment of the invention, the less visible tool portion is a thin outer portion of a surgical tool placed over an inner portion of a surgical tool, optionally in snug contact. In an exemplary embodiment of the invention, detection is made easier by presence of a gap (or other radio-visible feature, such as described below) between at least a portion of the thin outer portion and the inner portion. Optionally, the outer portion is provided as a sleeve which substantially contacts the inner portion of the tool at a widest portion thereof. In an exemplary embodiment of the invention, the inner tube has a generally cylindrical shape and is made of a radio-opaque material, for example, steel. In an exemplary embodiment of the invention, the tool is a bone access tool.

In an exemplary embodiment of the invention, the gap is formed near the distal end of the tool, for example, within 40 mm, 30 mm, 20 mm, 10 mm or intermediate or lesser amounts. In an exemplary embodiment of the invention, the positioning of the gap matches expected relative positioning of an outer cannula and a bone drill. Typically, the gap does not reach to the bone penetration section of such a drill or other tool. Optionally, the cannula and the drill are configured so that in usage the cannula cannot reach to the distal end of the drill in a mechanically locked position and/or have a locked position where it does not reach.

In an exemplary embodiment of the invention, absent the gap, it is difficult to distinguish presence of the outer portion over the inner portion due to its thinness and thus small increase in diameter. In an exemplary embodiment of the invention, the outer portion, for example, a tube, selectively blocks radiation that would otherwise pass through the gap. Alternatively or additionally, the gap is visible even when the outer portion is adjacent (albeit possibly less visible), and the contrast with the gap makes the outer portion more visible.

In an exemplary embodiment of the invention, the gap, when visualized under X-ray, indicates an amount of relative axial motion of the outer portion with respect to the inner portion. Optionally, the gap is marked so that a degree of coverage thereof can be assessed visually.

In an exemplary embodiment of the invention, the gap is formed by engraving, etching or otherwise modifying a cross section of the inner portion of the tool, optionally along a relatively short axial section thereof. Optionally, the gap is non-uniform in an axial and/or circumferential direction, for example, being in the form of a series of grooves, a series of indentations or bumps formed in a groove or a spiral shaped groove. In an exemplary embodiment of the invention, the gap comprises one or more circumferential indentations. In an exemplary embodiment of the invention, the tool has a same or similar diameter and/or radio-visible profile before and after the gap. Optionally, the gap itself has a relatively uniform profile/diameter.

Optionally, the gap is filled in so the surface of the inner portion is smooth.

In an exemplary embodiment of the invention, the outer portion of the tool comprises a cannula. Optionally, the cannula is provided as a sleeve adapted to fit over at least a portion of a reamer. In an exemplary embodiment of the invention, the cannula serves for injection of a bone filler and/or cement after removal of the reamer drill.

In an exemplary embodiment of the invention, the series of gaps are characterized by known axial dimensions with respect to reamer and are placed at known positions on the (e.g. at a known distance from a distal end of the reamer drill). Optionally, a user of the tool evaluates a position of an end of the cannula relative to the series of gaps. In an exemplary embodiment of the invention, this evaluation aids in inserting the cannula to a desired depth by helping to judge a distance from an anatomic landmark (e.g. cannula end is 12 mm from a distal side of a vertebra). Optionally, translational motion of the cannula with respect to the reamer can cover and/or uncover a portion of the gaps. In an exemplary embodiment of the invention, a number of exposed gaps is an indicator of relative axial position of the cannula with respect to the reamer drill.

In various exemplary embodiments of the invention, the tool is adapted for percutaneous spinal surgeries, such as fixation of vertebral body fractures or intervertebral disc surgeries (e.g. for gaining access into the disc). Optionally, a small difference in outer diameter between the reamer drill and the cannula makes it possible to insert the cannula and reamer drill together and/or minimize soft tissue and/or bone damage.

In other exemplary embodiments of the invention, the tool is used in treatment of non-vertebral bones.

An aspect of some embodiments of the invention relates to a device/kit, intended to gain an access into a body component, such as a bone or an intervertebral disc, comprising stylet/guide wire, reamer/drill and cannula.

In one embodiment of the invention, the device provides for a one-step access into, for example, a bone.

In another embodiment of the invention, the device components are assembled prior to use, and are inserted together into the bone. In an exemplary embodiment of the invention, the stylet/guide wire has a pointed distal end, and connection means to the reamer/drill at its proximal end. In another exemplary embodiment of the invention, the stylet/guide wire diameter is smaller than the internal diameter of the reamer/drill, and it is adapted to be introduced into the cannulated reamer/drill. Optionally, the stylet/guide wire is longer than the reamer/drill. In an exemplary embodiment of the invention, the reamer/drill comprises a distal section capable of reaming/drilling, respectively, the bone. At its proximal end, the reamer/drill may include a handle and connection means to the stylet/guide wire. In another embodiment of the invention, the cannula is assembled over the reamer/drill. In an exemplary embodiment of the invention, the cannula is shorter than the reamer/drill. Optionally, the cannula includes a handle at its proximal end. Optionally, the reamer/drill component has a section, located distally to the cannula while the cannula and reamer/drill are assembled, which is differentially visible on an x-ray image compared to the cannula. Optionally, said section is located partly distally to the cannula, while its proximal end is located within the distal portion of a cannula lumen. Thus, the distal end of the cannula can be easily distinguished from the reamer/drill body. This feature allows a minimal difference between cannula and reamer/drill diameters, and hence provides for a smaller total diameter of the device. Optionally, the reamer/drill is narrowed at said section. Optionally, the reamer/drill and/or cannula are made of radio-opaque material, for example stainless steel. Optionally, said reamer/drill small diameter section is covered by additional material, which is radiolucent and thus is visibly distinguished under fluoroscopy from the cannula.

Optionally, said radiolucent material is a polymer, for example polypropylene or ABS. Optionally, said radiolucent material is mold injected onto the reamer/drill small diameter section. Optionally, the covered section of the reamer/drill has the same diameter as the nearby sections of the reamer/drill body.

In yet another embodiment of the invention, the bone access assembly is constructed from biocompatible materials. In an exemplary embodiment of the invention, the components of the bone access assembly are made of, for example, metal, such as stainless steel, and/or polymer material. Optionally, the handle is made of polymer.

An aspect of some embodiments of the invention relates to a method, intended to provide a one-step access into a body organ, such as a bone. In an exemplary embodiment of the invention, said method is used in minimally invasive procedures. In another exemplary embodiment of the invention, the method is used in percutaneous spinal surgeries, such as fixation of vertebral body fractures. Alternatively, said method is used in intervertebral disc surgeries, e.g., for gaining access into the disc. In additional exemplary embodiment of the invention, said method is used in treatment of other bones.

In another embodiment of the invention, the procedure for gaining access into the body organ, such as a bone, is monitored by CT scanning and/or fluoroscopy.

In an exemplary embodiment of the invention, there is provided a device for gaining one-step access into a bone, comprising a stylet, a reamer and a cannula.

In an exemplary embodiment of the invention, there is provided a device for gaining one-step access into an intervertebral disc, comprising a stylet, a reamer and a cannula.

Optionally, the bone is a vertebral body.

In an exemplary embodiment of the invention, there is provided a method for accessing a vertebral body, wherein positioning of the insertion tool into the pedicle is done using a small diameter tool over which a larger diameter tool is positioned to continue the dilatation once a smaller diameter tool is well positioned.

In an exemplary embodiment of the invention, there is provided a "gaining access" device into a bone, comprising a reamer having a retractable distal tip, capable of forming a passage in a bone, over which the reamer and cannula are positioned in one step.

Optionally, the device is used in vertebroplasty and/or kyphoplasty procedures.

Optionally, the reamer component comprises a section located distally or partly distally to the cannula component while at least reamer and cannula are assembled, and where said reamer section is visibly distinguished from the cannula under fluoroscopy or other imaging means.

In an exemplary embodiment of the invention, there is provided a surgical apparatus, the apparatus comprising: (a) a cutting tool comprising an axial member with a proximal end and a distal end, the axial member characterized by at least two adjacent axial sections which do not form a part of a cutting tip of said tool, wherein differences between each of the sections are visually discernible when viewed in a projection x-ray image; and (b) a hollow tube adapted for parallel alignment with the cutting tool and selectively axially positionable to be adjacent at least a selective one of said axial sections and block x-ray radiation from at least one of passing through or passing adjacent said selected section so that said projection indicates a relative axial position of said hollow tube and said cutting tool.

Optionally, the cutting tool is adapted for bone access.

Optionally, the cutting tool is adapted for vertebral access.

Optionally, the hollow tube comprises a sleeve adapted to contain at least an axial portion of the cutting tool.

Optionally, the hollow tube comprises a partial sleeve which does not circumferentially surround the cutting tool, adjacent said section.

Optionally, the sleeve has an inner diameter which is adapted to ensure substantial contact with said cutting tool.

Optionally, the hollow tube blocks said radiation from at least part of said selective section.

Optionally, the hollow tube blocks said radiation from an area adjacent said selected section.

Optionally, the visually discernible difference results from an outer radial section of reduced radio-opacity.

Optionally, the outer radial section comprises a filled-in groove.

Optionally, the cutting tool comprises at least one radially distal hollow.

Optionally, the radially distal hollow does not reach a distal end of said cutting tool.

Optionally, the visually discernible differences are rotationally symmetric, with respect to rotation of said cutting tool and said hollow tube with respect to said x-ray radiation.

Optionally, the visually discernible differences are each axially uniform.

Optionally, the at least one of the axial sections comprises an axially varying profile.

Optionally, the axially varying profile comprises a series of axially separated decreased radio-opaque diameter portions.

Optionally, at least one of said axial sections comprises an axially extending spiral of at least partly radio-opaque material.

Optionally, the cutting tool comprises an inner lumen.

Optionally, the cutting tool can operate with a guide element, optionally provided as part of the apparatus, adapted for insertion through the inner lumen.

Optionally, the cutting tool comprises a bone penetrating element and said hollow tube comprises a bone cannula.

Optionally, the bone cannula has a wall thickness of 0.4 mm or less.

Optionally, the bone cannula has a wall thickness of 0.3 mm or less.

In an exemplary embodiment of the invention, there is provided a method for discerning relative axial displacement of two tool portions under X-ray, the method comprising: (a) inserting a first tool portion having at least two sections with different X-ray silhouettes into a bone; (b) positioning a second tool portion adjacent a first one of said sections in a manner which does not alter an appearance of a silhouette of said first one of said section; and (c) axially relatively repositioning said second tool portion adjacent a second one of said sections in a manner which alter an appearance of a silhouette of said second one of said sections.

Optionally, the bone is a vertebra.

Optionally, the method comprises determining a relative axial location of said second tool portion relative to said first tool portion based on a change in a visualization of said second section.

Optionally, the determining comprises counting visually identifiable x-ray markers.

Optionally, the second tool comprises a cannula and the method comprises determining a correct placement of said cannula relative to a bone based on said determining.

Optionally, the determining comprises ascertaining a reduction in an axial extent of said second section.

In an exemplary embodiment of the invention, there is provided a method for locating a hollow radio-opaque tube adjacent or inside a bone, the method comprising:

(a) inserting a first element into a bone, said element comprising both radio-opaque and radiolucent portions; and (b) positioning said radio-opaque hollow tube adjacent to the first element so that a relative position of the radio-opaque hollow tube and a radiolucent portion is visible in an image acquired using non-invasive imaging equipment.

Optionally, the non invasive imaging equipment employs X-ray.

BRIEF DESCRIPTION OF THE FIGURES

Some exemplary embodiments of the invention will be further described with reference to the accompanied drawings, in which same number designations are maintained throughout the figures for each element and in which:

FIGS. 9A and 9B are cross sectional side views of apparatus including a radiolucent and/or radio-transparent marking section according to exemplary embodiments of the invention.

DETAILED DESCRIPTION OF EXEMPLARY EMBODIMENTS

Figure 1:
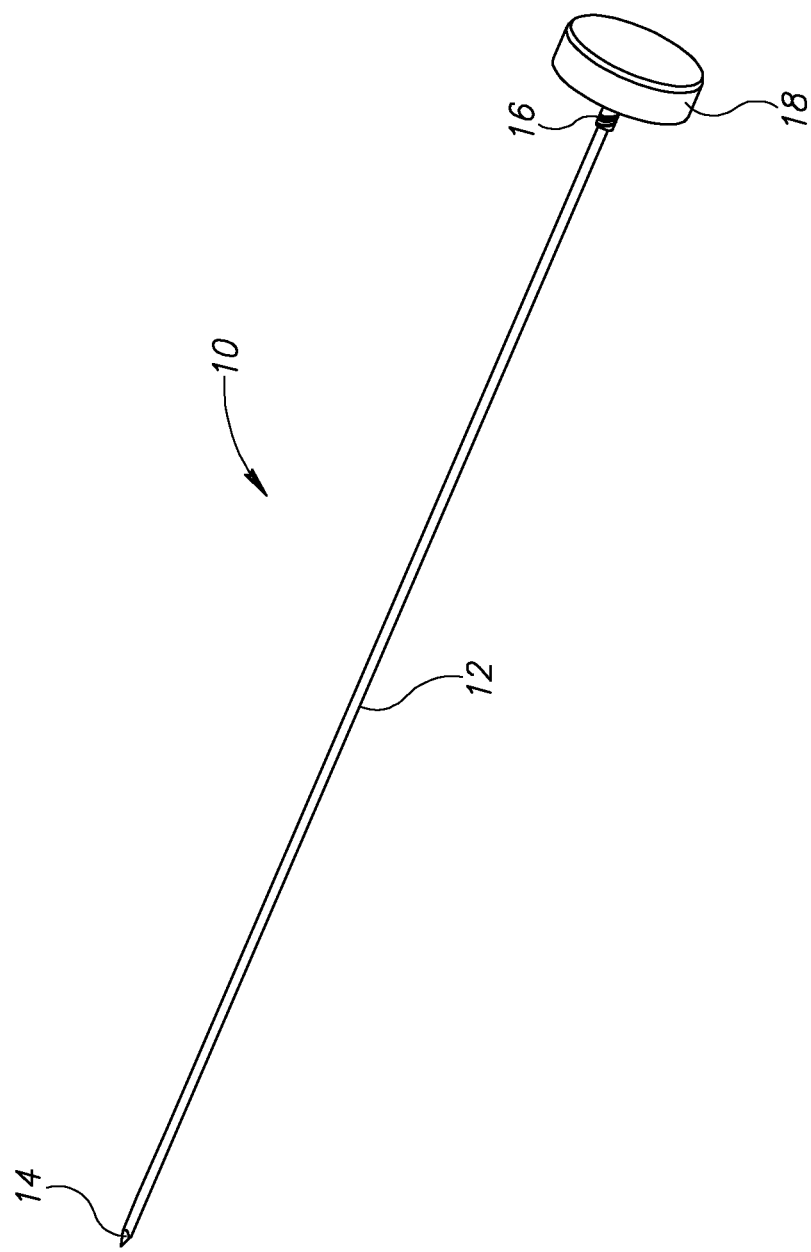
FIG. 1 is a perspective view of an exemplary stylet component of an exemplary bone access device, in accordance with some exemplary embodiments of the invention.
Figure 2:
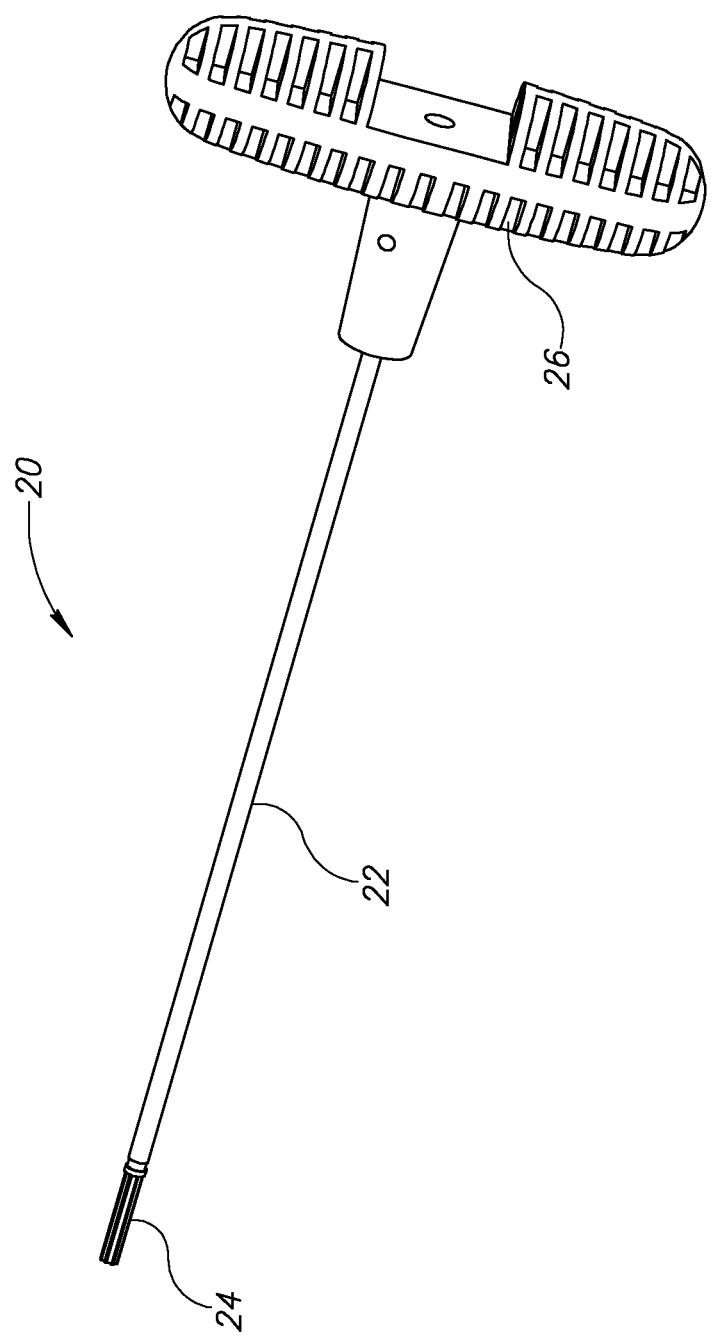
FIG. 2 is a perspective view of an exemplary reamer component of an exemplary bone access device, in accordance with some exemplary embodiments of the invention.

FIG. 1 illustrates an exemplary stylet 10 suitable for an exemplary bone access device 40 (FIG. 4), in accordance with some exemplary embodiments of the invention. Optionally, stylet 10 can be replaced by a guidewire. Stylet 10 is depicted as a tubular rod 12, having a pointed distal end 14 adapted to puncture and penetrate skin, soft tissue and/or cortical bone. Distal end 14 may be, for example, of diamond type, bevel type or J-type. Exemplary embodiments of stylet 10 designed for use with fractured vertebral body are optionally characterized by a diameter of about 1.4-2.2 mm. These exemplary embodiments of stylet 10 can optionally be inserted into the vertebral pedicle (up to about 2 mm in the vertebral body). In an exemplary embodiment of the invention, a proximal end of stylet 10 includes a thread 16. Optionally, thread 16 is compatible with matching threads on a reamer 20 (FIG. 2). In an exemplary embodiment of the invention, thread 16 is operable during assembly of stylet 10 and reamer 20 components.

Optionally, rotation of a head 18 of stylet 10 serves to rotate threads 16. Alternative connecting/interlocking mechanisms may be used as well, for example as described below with respect to FIGS. 7A and 7B.

Figure 4:
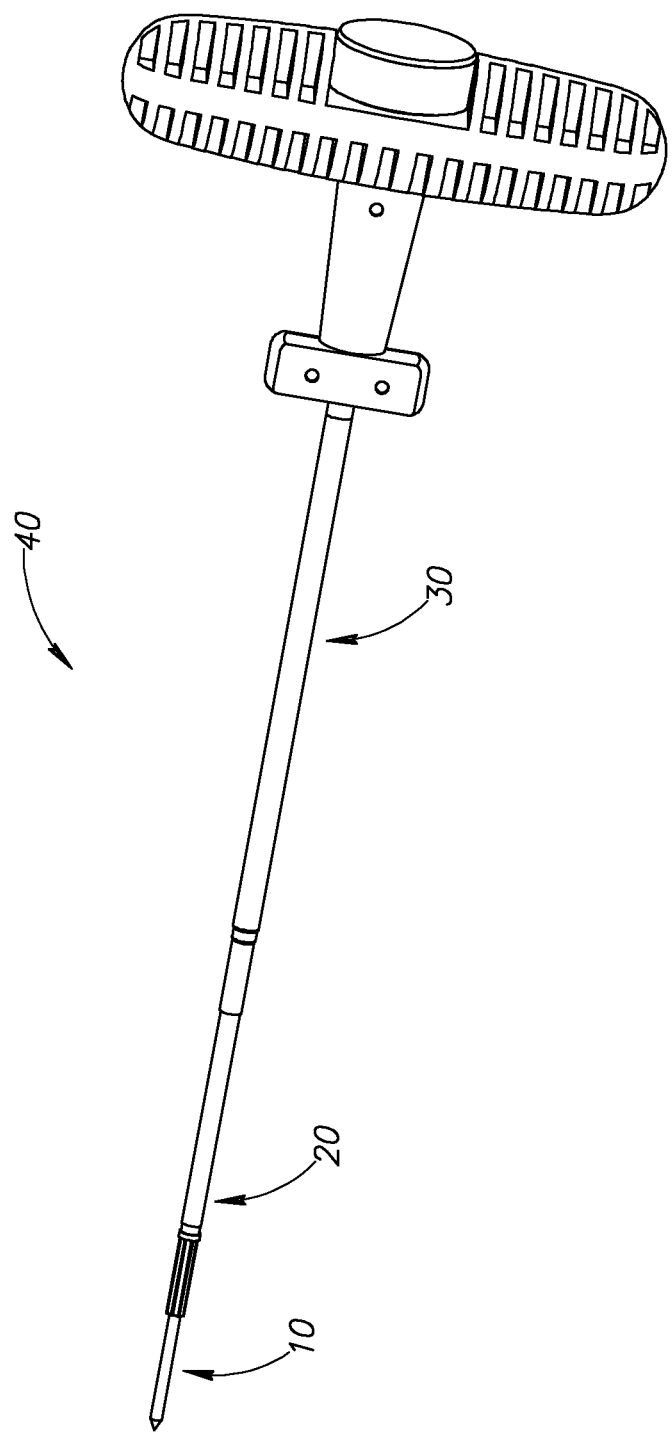
FIG. 4 is a perspective view of an exemplary bone access device, in accordance with some exemplary embodiments of the invention.

FIG. 2 illustrates an exemplary reamer 20 suitable for exemplary bone access device 40 (FIG. 4). In the depicted embodiment, reamer 20 comprises a tubular body 22, a reamer-like distal end 24, and a handle 26. Optionally, distal end 24 is adapted for drilling. Optionally, a proximal section of reamer 20 includes a thread (not shown in FIG. 2), for connection of reamer 20 and stylet 10. In an exemplary embodiment of the invention, a lumen of reamer 20 is adapted to accommodate stylet 10. Optionally, the lumen of reamer 20 has an inner diameter slightly larger than an outer diameter of stylet 10. In some exemplary embodiments of apparatus 40 adapted for use in spinal surgery, the outer diameter of the reamer may be 3, 4, 5 or 6 mm or lesser or intermediate diameters. Optionally, reamer 20 is shorter than stylet 10 so that stylet 10 protrudes from distal end 24 of reamer 20 when head 18 of stylet 10 engages handle 26 of reamer drill 20.

Figure 3:
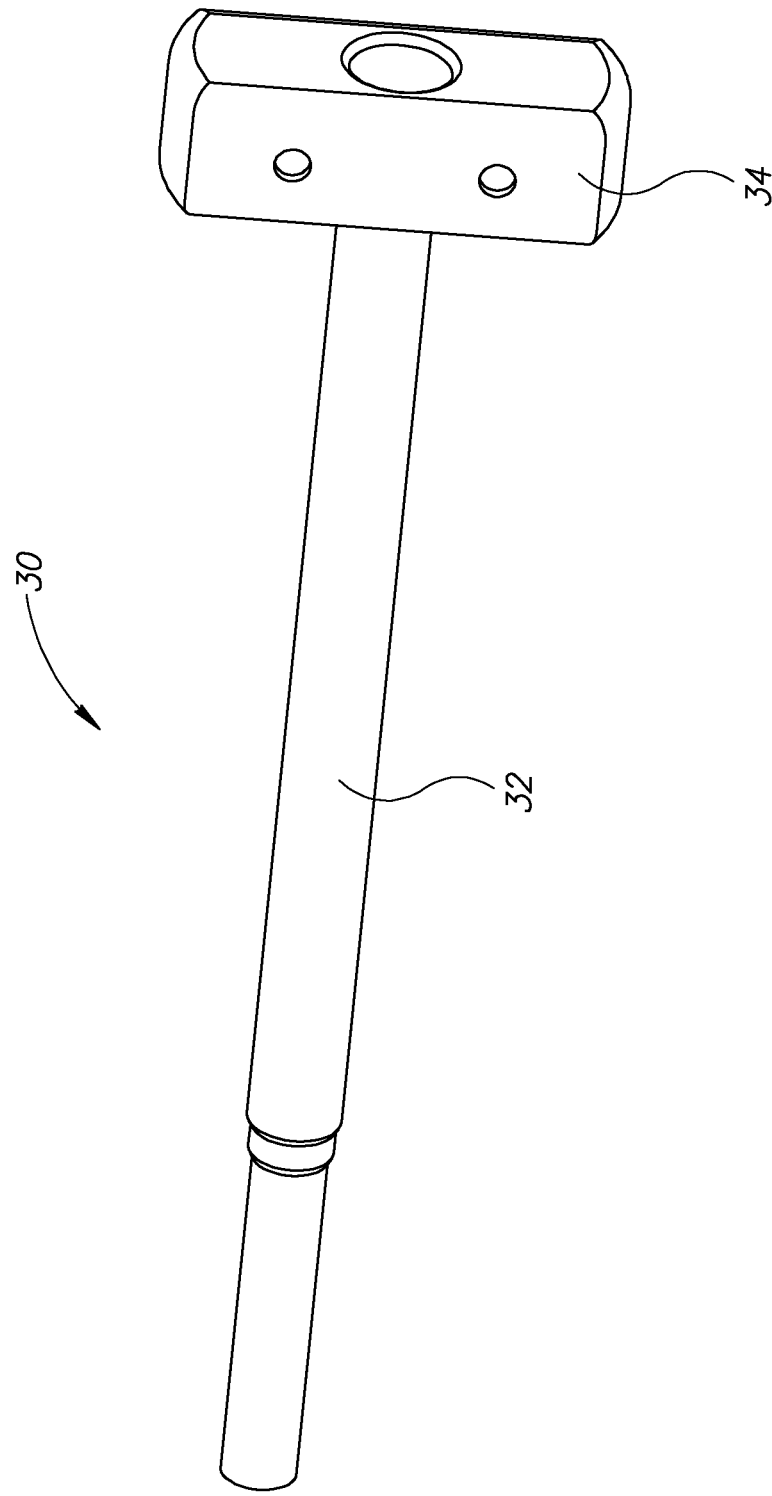
FIG. 3 is a perspective view of an exemplary cannula component of an exemplary bone access device, in accordance with some exemplary embodiments of the invention.

FIG. 3 illustrates an exemplary cannula 30 suitable for use as part of exemplary bone access device 40. In an exemplary embodiment of the invention, cannula 30 comprises a tubular body 32 and a handle 34. Optionally, reamer 20 is adapted for insertion into cannula 30 so that tubular body 32 of cannula 30 substantially conforms to axial member 22 of reamer drill 20. In an exemplary embodiment of the invention, cannula 30 is shorter than reamer 20. Optionally, when reamer 20 is inserted in cannula 30 so that handle 34 of cannula 30 is adjacent to handle 26 of reamer 20, distal portion 24 of reamer 20 protrudes from cannula 30. Optionally, the outer surface of cannula 30 slightly tapers at its distal portion to facilitate insertion of cannula 30 into bone.

FIG. 4 illustrates exemplary stylet 10, exemplary reamer 20, and exemplary cannula 30 assembled to form exemplary bone access device 40.

Figure 5A:
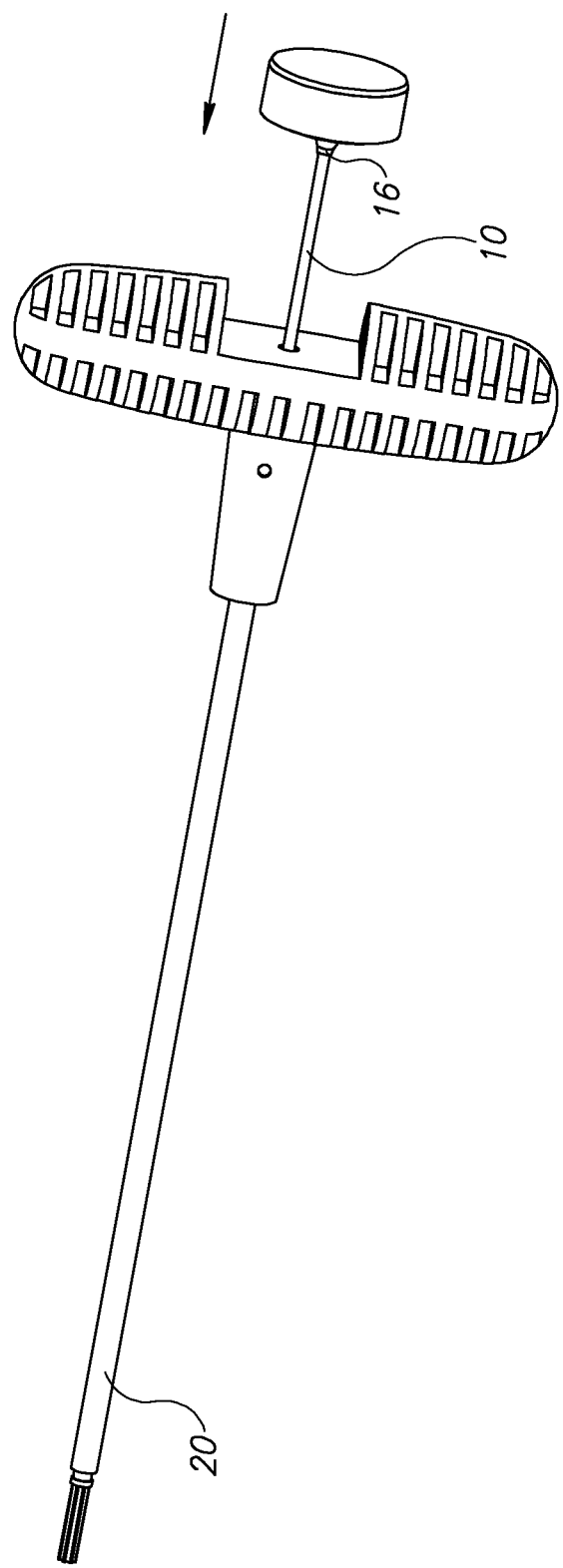
FIGS. 5A, 5B and 6 illustrate an exemplary assembly of an exemplary bone access device, in accordance with some exemplary embodiments of the invention.
Figure 5B:
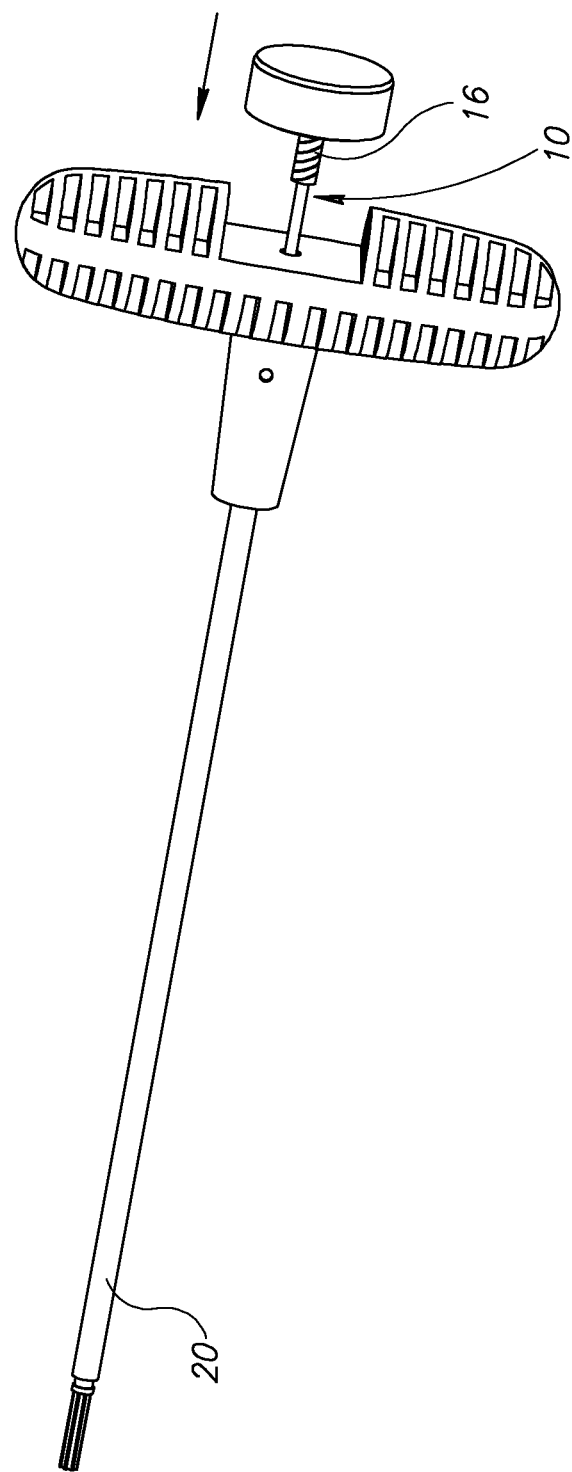
Figure 6:
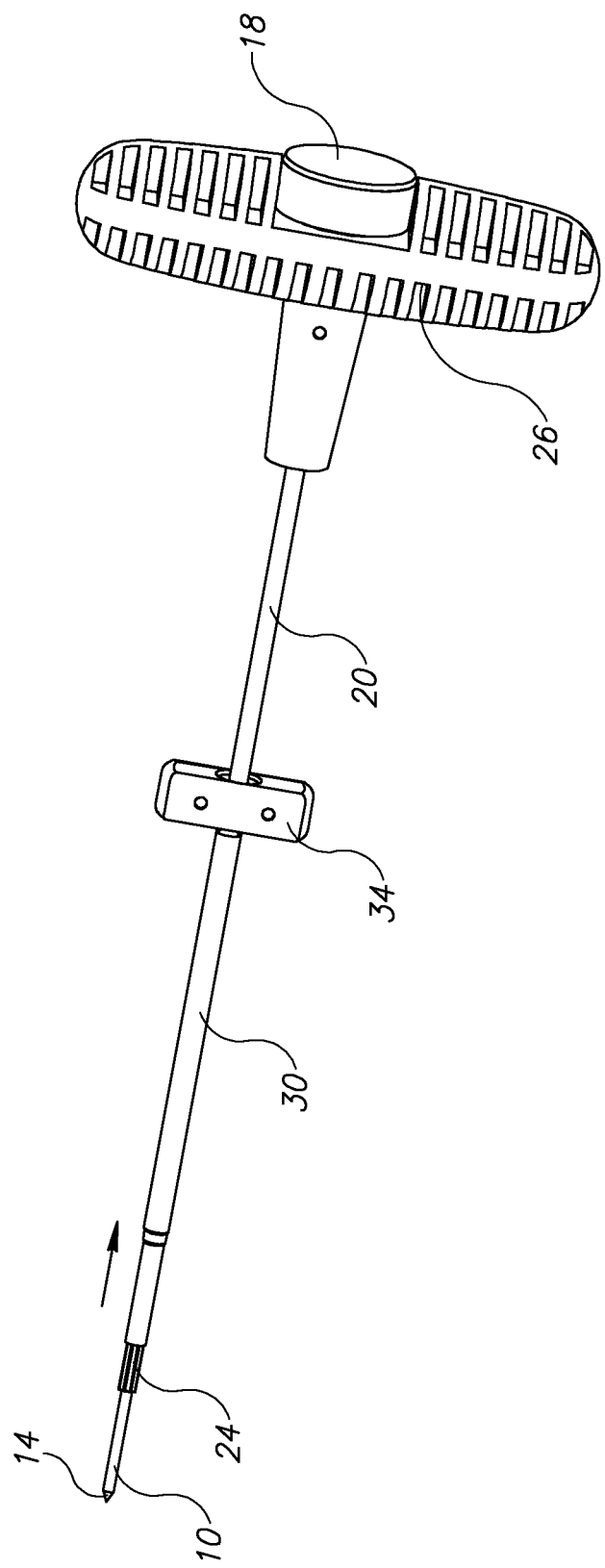

Referring now to FIGS. 5A, 5B and 6, exemplary assembly of bone access device 40 is described in detail. As can be seen in FIGS. 5A and 5B, stylet 10 can be inserted into reamer 20, through a proximal end of the reamer 20, in the arrow direction. Stylet 10 and reamer 20 are threaded and locked together, optionally by clockwise rotation of the stylet 10 and threads 16. Optionally, stylet thread 16 can be made sufficiently long (FIG. 5B) to allow a user to control an amount of stylet 10 which protrudes from a distal end 24 of reamer 20 (optionally none, in some stages of use).

In an exemplary embodiment of the invention, device 40 is configured for vertebral body treatment and about 20 mm of stylet 20 protrudes from distal end 24 of reamer 20 after assembly (FIG. 6).

In other exemplary embodiments of the invention, relative sizes of stylet 10, reamer 20 and cannula 30 may differ.

FIG. 6 depicts connection of cannula 30 to already-assembled stylet 10 and reamer 20. In the depicted embodiment, cannula 30 is assembled over reamer 20, in the arrow direction, until cannula handle 34 is adjacent to reamer handle 26.

In an exemplary embodiment of the invention, once assembly as described above is complete, accessing of a vertebral body is undertaken. Optionally, access is conducted under fluoroscopy. Initially, device 40 can be inserted into a vertebra so that pointed distal tip 14 of stylet 10 penetrates the skin, soft tissue and vertebra pedicle. Optionally, penetration at this stage is a few millimeters into the vertebral body.

In an exemplary embodiment of the invention, the accessing of the vertebral body is by a transpedicular approach. Optionally, stylet tip 14 passes through the entire pedicle, along its axial midline. At this stage, handle 26 of reamer 20 can optionally be slightly rotated in each direction. In an exemplary embodiment of the invention, this slight bidirectional rotation (or single-directional rotation) serves to ream and/or drill the bone, and/or to advance reamer 20 slightly into the vertebral body.

At this stage, stylet 10 can optionally be disconnected (e.g. by unthreading) or partly disconnected from reamer 20. Disconnection of stylet 10 prior to reaming and/or drilling of the bone optionally prevents undesired advancement of stylet 10 beyond a desired depth. If stylet 10 has been previously partially disconnected, disconnection can be completed at this stage and stylet 10 can be removed.

In an exemplary embodiment of the invention, reamer 20 is employed for additional drilling at this stage. Optionally, the additional drilling proceeds until distal end 24 of reamer 20 is about 2-3 mm from an anterior cortex. Optionally, the distance is assessed by fluoroscopy. In an exemplary embodiment of the invention, cannula 30 is advanced over reamer 20 at this stage. Optionally, advancement of cannula 30 continues until cannula 30 penetrates the pedicle to a depth of about 2 mm. Optionally, the gap (FIG. 9) is positioned to be at the entrance to the pedicle or in cortical bone thereof, to make this penetration depth more visible. Cannula 30 may optionally be gently hammered to achieve a desired penetration. At this time, the reamer is optionally removed. In an exemplary embodiment of the invention, the operation may proceed via the cannula.

Figure 7:
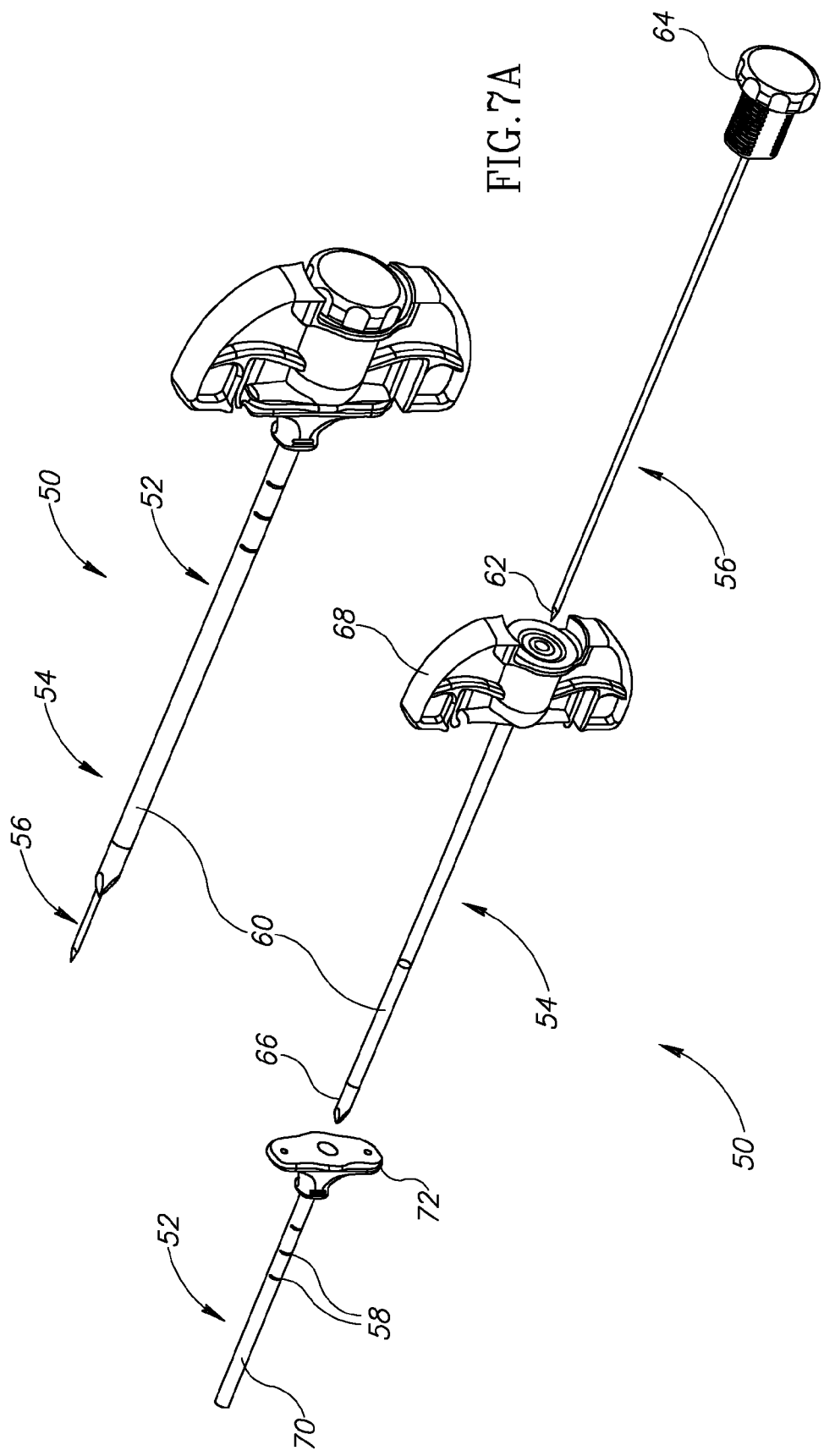
FIGS. 7A and 7B illustrate an alternative bone access device, in accordance with an exemplary embodiment of the present invention.

FIGS. 7A and 7B illustrate alternative exemplary embodiments 50 of a bone access device.

FIG. 7A depicts an assembled device 50, comprising a cannula 52, a drill 54, and a guide wire 56.

FIG. 7B is an exploded view of device 50 of FIG. 7A. Optional guide wire 56 is depicted as a tubular rod with a pointed distal end 62 adapted to puncture and/or penetrate skin, soft tissue and cortical bone. Distal end 62 may be, for example, of diamond type, bevel type or J-type. In an exemplary embodiment of the invention, guide wire 56 fits into a lumen of drill 54.

In an exemplary embodiment of the invention, configured for use in a fractured vertebral body, guide wire 56 may be characterized by a diameter of about 1.4-2.2 mm. Optionally, this configuration allows insertion of tip 62 of guidewire 56 into a vertebral pedicle (e.g., up to about 2 mm in the vertebral body).

Optionally, guidewire 56 includes a knob or other control 64 for selective advancing and/or retracting guide wire 56 relative to drill 54.

Exemplary drill tool 54 of device 50 includes an elongate body with a distal end 66 adapted for drilling, and a handle 68. The body of drill 54 fits in the lumen of cannula 52. Optionally, the design of tips 62 and 66 are matched to provide a desirable bone penetrating behavior, optionally acting as a single bit. Optionally, the bone type and/or penetration desired determined the allowed extension of tip 62 past tip 66.

In an exemplary embodiment of the invention, drill 54 has a section 60, located distally to cannula 52 when device 50 is assembled, which contributes to distinguishing between drill 54 and cannula 52 in an x-ray image as cannula 52 advances towards distal tip 66 drill 54. In an exemplary embodiment of the invention, covering a portion of section 60 by cannula 52 contributes to determining a position of a distal tip of cannula 52 (see FIG. 9 below).

In an exemplary embodiment of the invention, drill 54 is characterized by an outer diameter of 2, 3, 4, 5 or 6 mm or lesser or greater or intermediate diameters. Optionally, cannula 52 is configured as a sleeve with a thickness of less than 0.5, optionally less than 0.4, optionally less than 0.3 mm. In an exemplary embodiment of the invention, the outer portion of the tool is provided as a cannula with an inner diameter of about 2.7 mm and an outer diameter of about 3 mm.

In an exemplary embodiment of the invention, use of section 60, in which radio-opacity is reduced on an outside of drill 54, contributes to detection of a minimal difference in change of outer diameter of device 50. Optionally, an axial position at which a change in outer diameter of device 50 occurs is readily discernible in an X-ray image, by the change being relative to a reduced radio-opaque diameter at section 60, rather than the regular radio-opaque diameter at other parts (see FIG. 9). Optionally, reduction in reliance on cannula thickness to determine cannula position makes it possible to construct a cannula 52 with a smaller outer diameter, for example, 0.25 mm, 0.2 mm or less.

In an exemplary embodiment of the invention, drill 54 and/or cannula 52 are made of radio-opaque metal (e.g. stainless steel and/or aluminum). Optionally, section 60 includes radiolucent or radio-transparent material such as a polymer (e.g. polypropylene or ABS).

Optionally, drill section 60 comprises at least one small diameter metal region. Optionally, the small diameter metal region is covered by radiolucent or radio-transparent material. Optionally, radiolucent or radio-transparent material is mold injected onto relevant portions of section 60.

In an exemplary embodiment of the invention, an outer diameter of drill section 60 is similar to an outer diameter of adjacent portions of drill 54. Optionally, a drill 54 for spinal surgery, is characterized by an outer diameter of about 4-5 mm, or less.

In an exemplary embodiment of the invention, cannula 52 comprises a tubular body 70, and a handle 72. Optionally, the cannula 52 slightly tapers at its distal portion to facilitate its insertion into the bone. Optionally, cannula 52 comprises depth markings 58. Optionally, drill handle 68 selectively rotationally locks to cannula handle 72, for manipulation using a single hand, optionally using a snap-lock. Optionally, the snap-lock locks in one rotation direction and unlocks in another. Other interlocking mechanisms may be used.

Figure 8:
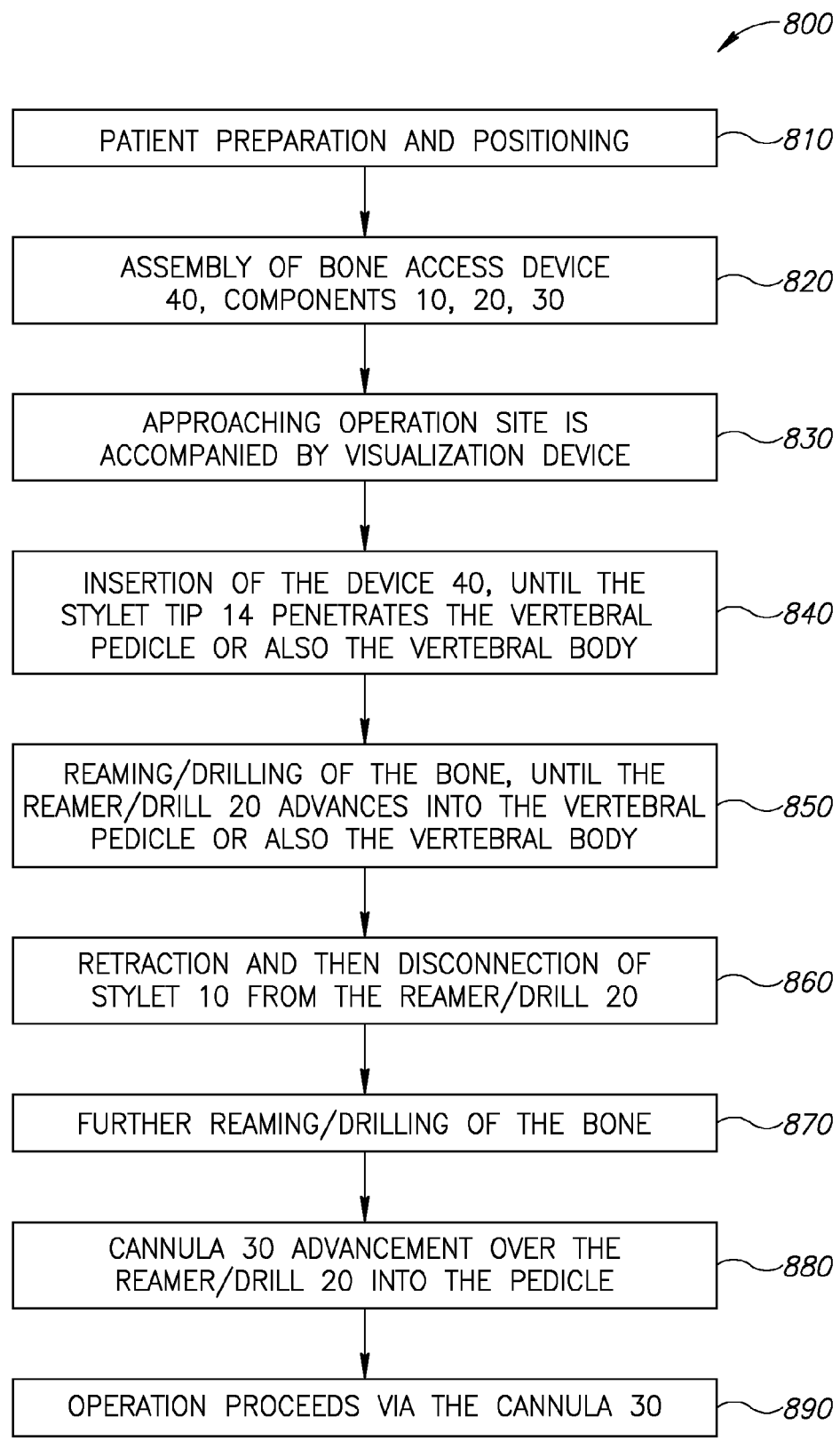
FIG. 8 is a simplified flow diagram illustrating an exemplary sequence of events associated with use of some embodiments of the invention.

FIG. 8 is a simplified flow diagram 800 of a method of employing apparatus 40 in a surgical procedure, in accordance with an exemplary embodiment of the invention.

At 810 a patient is prepared and positioned.

At 820 an exemplary bone access device 40 is assembled as described hereinabove.

At 830, a visualization device (e.g. an X-ray camera or fluoroscopy device) is provided to monitor an approach of apparatus 40 to an operation site.

At 840, apparatus 40 is inserted, optionally until stylet tip 14 reaches a desired location. Optionally, the visualization device indicates when the desired location has been reached.

At 850, reamer drill 20 is advanced until penetration to a desired location is achieved. Optionally, the visualization device indicates when the desired penetration has been achieved.

At 860, stylet 10 is retracted and removed from reamer drill 20.

At 870, reaming/drilling is optionally continued.

At 880, cannula 30 is advanced over reamer/drill 20, optionally into the pedicle. At this stage, a position of a distal end of cannula 30 is optionally ascertained and/or adjusted using the visualization device. Optionally, ascertaining a position indicates ascertaining a relative position of cannula 30 with respect to reamer drill 20 as described in greater detail below with reference to FIGS. 9A and 9B. Optionally, reamer drill 20 is removed from cannula 30.

At 890 cannula 30 is employed to conduct a desired surgical procedure. For example, injection of a bone filler and/or cement via cannula 30 may be undertaken to affect vertebroplasty.

FIGS. 9A and 9B are cross sectional side views of exemplary embodiments 900 and 950, respectively of apparatus 40 and in particular radiolucent and/or radio-transparent marking section 60 thereof. In each of these figures, a distal end 14 of stylet 10 is seen protruding beyond a reamer-like distal end 24 of body 22 of reamer 20. Tubular body 32 of cannula 30 is shown assembled on body 22 of reamer drill 20.

FIG. 9A depicts an exemplary embodiment 900 of apparatus 40 in which a single groove 910, pictured as a circumferential groove, is formed in body 22 of reamer drill 20. Formation of groove 910 may be accomplished by any means known in the art including, but not limited to, etching, engraving, die casting, carving and lathe turning. Groove 910 represents one exemplary embodiment of section 60 as described hereinabove.

In an exemplary embodiment of the invention, the groove terminates, in a distal direction, in a diameter increasing section, so that two steps are visible in x-ray imaging, one when entering the groove at a first axial position and a second one when exiting the groove. Optionally, the diameter at the two steps is the same and matches the inner diameter of the cannula.

In FIG. 9A an optional radio-transparent or radiolucent filling 920 is shown filling groove 910. In an exemplary embodiment of the invention, radiolucent filling 920 makes advancement of a leading edge 31 of body 32 of cannula 30 over groove 910 easier. In cases where the leading edge is not radio-opaque, a location of a radio-opaque section (e.g., ring or other marker) of cannula 30 may be detected.

In an exemplary embodiment of the invention, construction of body 22 of reamer 20 is conducted according to an engineering plan so that dimensions of groove 910 (e.g. axial length and depth) are known. In addition, the engineering plan specifies a distance between groove 910 and reamer-like distal end 24 of body 22 of reamer 20.

As tubular body 32 of cannula 30 advances along body 22 of reamer 20, leading edge 31 of tubular body 32 progressively covers an increasing portion of groove 910. In an exemplary embodiment of the invention, an X-ray based imaging modality (e.g. fluoroscopy) is used to monitor progress of leading edge 31 of tubular body 32 with respect to groove 910.

In some exemplary embodiments of the invention, at least a portion of tubular body 32 is radio-opaque with respect to the chosen imaging modality. According to these exemplary embodiments of the invention, as leading edge 31 advances, an increasing portion of groove 910 is obscured. As a result, a fluoroscopy image acquired laterally (or otherwise non-axially) will indicate an apparent decrease in an axial length of groove 910 as edge 31 advances towards distal end 24 of body 22 of reamer drill 20. Optionally, a portion of tubular body 32 is substantially radio-transparent and the radio-opaque portion is used to determine relative axial position of tubular 32 with respect to reamer 20.

In other exemplary embodiments of the invention, tubular body 32 is relatively radiolucent with respect to the chosen imaging modality. According to these exemplary embodiments of the invention, as leading edge 31 advances, an increasing portion of groove 910 is covered, but not completely obscured. As a result, a fluoroscopy image acquired laterally will indicate a division of groove 910 into two zones. A first zone inside tubular body 32 will be subject to decreased X-ray transmission and will appear lighter. A second zone, outside tubular body 32 will not be subject to decreased X-ray transmission and will appear darker. Optionally, even if body 32 is relatively radiolucent so that a regular thickness thereof does not hide the groove, it is noted that a portion of the tube has a greater thickness in the x-ray imaging direction, and that portion may be visible against the contrast with the groove and the nearby portion 24.

Because details of the engineering plan of body 22 of reamer 20 are known, determination of a position of edge 31 of tubular body 32 of cannula 30 can optionally be translated into a determination of a distance from edge 31 to distal end 24 of body 22 of reamer 20. Optionally, this translation is useful in determining a position of edge 31 relative to anatomic landmarks in a bone in which reamer drill 20 has been inserted.

FIG. 9B shows an additional embodiment 950 of apparatus 40 in which a groove 908 formed in body 22 of reamer drill 20 is divided axially by protrusions 912. According to various exemplary embodiments of the invention, protrusions 912 may comprise individual rings or a spiral extending axially along body 22 of reamer 20. Optionally, protrusions 912 result from formation of groove 912 or are applied after groove 908 is applied. Filling with radio-lucent material is optionally provided.

In those exemplary embodiments of the invention in which protrusions 912 are provided as individual rings, groove 908 is divided into a plurality of grooves.

In those exemplary embodiments of the invention in which protrusions 912 are provided as a spiral extending axially along body 22 of reamer 20, groove 908 can be a spiral groove extending axially along body 22 of reamer 20.

In those exemplary embodiments of the invention which include protrusions 912, advancement of edge 31 of tubular body 32 produces a series of covered portions 930 of groove 908. In an exemplary embodiment of the invention, each space between adjacent protrusions 912 represents an axial length of body 22 of reamer drill 20. As the number of covered portions 930 increases, the number of spaces between adjacent protrusions 912 in front of edge 31 decreases. In an exemplary embodiment of the invention, counting of spaces between adjacent protrusions 912 in front of edge 31 can be used to calculate a distance between edge 31 and distal end 24 of reamer 20. Optionally, this counting is useful in determining a position of edge 31 relative to anatomic landmarks in a bone in which reamer drill 20 has been inserted.

The method described above is not limited to spinal procedures and to bones. In addition, other geometries than a sleeve on a cylinder may be used. For example, the inner-tool portion may be a rectangular in cross-section. In another example, the sleeve may not cover an entire circumference of the cylinder. In another example, the less visible tool section rides in a slot in the more visible tool portion and is made visible by the more visible tool portion including an area adjacent the slot which is radiolucent.

Components of apparatus 40 are not necessarily limited by exemplary dimensions recited above. Recited dimensions are exemplary only, and may vary and/or become part of a range of dimensions.

Various features of exemplary embodiments of the invention have been described in the context of a device, apparatus or a method. It should be appreciated that combinations of the above features are also considered to be within the scope of the invention. In addition, features described in the context of a device or apparatus may be employed to characterize exemplary methods according to the invention. Alternatively or additionally, features described in the context of a method may be employed to characterize exemplary devices or apparatus according to the invention. It should also be appreciated that some of the embodiments are described only as methods or only as apparatus, however the scope of the invention includes both methods for using apparatus and apparatus for applying methods. The scope of the invention also covers machines for creating the apparatus described herein. In addition, the scope of the invention also includes methods of using, constructing, calibrating and/or maintaining the apparatus described herein. When used in the following claims or in the text above, the terms "comprises", "comprising", "includes", "including" or the like mean "including but not limited to".

The invention claimed is:

1. A surgical apparatus, the apparatus comprising:
   (a) a cutting tool comprising an axial member with a proximal end and a distal end, the axial member characterized by at least two adjacent axial sections which do not form a part of a cutting tip of said tool, wherein differences between each of the sections are visually discernible when viewed in a projection x-ray image, wherein said visually discernible difference results from an outer radial section of reduced radio-opacity; and
   (b) a hollow tube adapted for parallel alignment with the cutting tool and selectively axially positionable to be adjacent at least a selective one of said axial sections and block x-ray radiation from at least one of passing through or passing adjacent said selected section so that said projection image indicates a relative axial position of said hollow tube and said cutting tool.

2. Apparatus according to claim 1, wherein the cutting tool is adapted for bone access.

3. Apparatus according to claim 2, wherein the cutting tool is adapted for vertebral access.

4. Apparatus according to claim 1, wherein said hollow tube comprises a sleeve adapted to contain at least an axial portion of the cutting tool.

5. Apparatus according to claim 4, wherein said sleeve has an inner diameter which is adapted to ensure substantial contact with said cutting tool.

6. Apparatus according to claim 1, wherein said hollow tube comprises a partial sleeve which does not circumferentially surround the cutting tool adjacent said sections.

7. Apparatus according to claim 1, wherein said hollow tube blocks said radiation from at least part of said selected section.

8. Apparatus according to claim 1, wherein said hollow tube blocks said radiation from an area adjacent said selective section.

9. Apparatus according to claim 1, wherein said outer radial section comprises a filled-in groove.

10. Apparatus according to claim 1, wherein said cutting tool comprises at least one radially distal hollow.

11. Apparatus according to claim 10, wherein said radially distal hollow does not reach a distal end of said cutting tool.

12. Apparatus according to claim 1, wherein said visually discernible differences are rotationally symmetric, with respect to rotation of said cutting tool and said hollow tube with respect to said x-ray radiation.

13. Apparatus according to claim 1, wherein said visually discernible differences are each axially uniform.

14. Apparatus according to claim 1, wherein at least one of the axial sections comprises an axially varying profile.

15. Apparatus according to claim 14, wherein the axially varying profile comprises a series of axially separated decreased radio-opaque diameter portions.

16. Apparatus according to claim 1, wherein at least one of said axial sections comprises an axially extending spiral of at least partly radio-opaque material.

17. Apparatus according to claim 1, wherein the cutting tool comprises an inner lumen.

18. Apparatus according to claim 17, comprising a guide element adapted for insertion through the inner lumen.

19. Apparatus according to claim 1, wherein said cutting tool comprises a bone penetrating element and said hollow tube comprises a bone cannula.

20. Apparatus according to claim 19, wherein said bone cannula has a wall thickness of 0.4 mm or less.

21. Apparatus according to claim 20, wherein said bone cannula has a wall thickness of 0.3 mm or less.

* * * * *